US010012640B2

(12) United States Patent
Pant et al.

(10) Patent No.: US 10,012,640 B2
(45) Date of Patent: Jul. 3, 2018

(54) CELL CULTURE DEVICE WITH AN ARRAY OF MICROFLUIDIC NETWORKS

(71) Applicant: CFD Research Corporation, Huntsville, AL (US)

(72) Inventors: Kapil Pant, Huntsville, AL (US); Balabhaskar Prabhakarpandian, Madison, AL (US)

(73) Assignee: CFD RESEARCH CORPORATION, Huntsville, AL (US)

( * ) Notice: Subject to any disclaimer, the term of this patent is extended or adjusted under 35 U.S.C. 154(b) by 175 days.

(21) Appl. No.: 14/768,154

(22) PCT Filed: Feb. 14, 2014

(86) PCT No.: PCT/US2014/016506
§ 371 (c)(1),
(2) Date: Aug. 14, 2015

(87) PCT Pub. No.: WO2014/127250
PCT Pub. Date: Aug. 21, 2014

(65) Prior Publication Data
US 2015/0377861 A1    Dec. 31, 2015

Related U.S. Application Data

(60) Provisional application No. 61/764,941, filed on Feb. 14, 2013.

(51) Int. Cl.
*C12M 1/00* (2006.01)
*C12M 3/00* (2006.01)
(Continued)

(52) U.S. Cl.
CPC ........ *G01N 33/5008* (2013.01); *B01L 3/5025* (2013.01); *B01L 3/502715* (2013.01);
(Continued)

(58) Field of Classification Search
CPC ...... C12M 21/08; C12M 23/40; C12M 23/12; B01L 2200/0605; B01L 3/502715; B01L 3/50273

See application file for complete search history.

(56) References Cited

U.S. PATENT DOCUMENTS 6,908,767 B2 * 6/2005 Bader .................. B01L 3/5025
435/286.1
2003/0017142 A1 * 1/2003 Toner .................. A61M 1/3472
424/93.7

(Continued)

OTHER PUBLICATIONS

International Search Report and Written Opinion of the International Searching Authority; filed Feb. 14, 2014 PCT/US2014/016506.

*Primary Examiner* — Nathan A Bowers
(74) *Attorney, Agent, or Firm* — Maschoff Brennan

(57) ABSTRACT

A cell culture assay device can include: a substrate having a plurality of discrete microfluidic networks and a plurality of wells over the discrete microfluidic networks, each discrete microfluidic network having one or more wells fluidly coupled thereto, the wells extending upward from the discrete microfluidic networks; and a manifold body coupled with the substrate and having at least one fluid conduit pair for each microfluidic network and/or each well, each fluid conduit pair including a fluid inlet conduit and a fluid outlet conduit fluidly coupled to a corresponding microfluidic network and/or well. The substrate can be formed from a substrate base having the microfluidic networks coupled to a well plate having the wells associated with the microfluidic networks.

28 Claims, 24 Drawing Sheets

(51) Int. Cl.
*B01L 3/00* (2006.01)
*G01N 33/50* (2006.01)
*C12M 3/06* (2006.01)
*C12M 1/12* (2006.01)
*C12M 1/34* (2006.01)
*C12M 1/36* (2006.01)
*C12M 1/42* (2006.01)

(52) U.S. Cl.
CPC ............ *C12M 23/16* (2013.01); *C12M 23/34* (2013.01); *C12M 25/14* (2013.01); *C12M 29/00* (2013.01); *C12M 29/04* (2013.01); *C12M 41/00* (2013.01); *C12M 41/48* (2013.01); *B01L 2300/0829* (2013.01); *B01L 2300/0861* (2013.01); *B01L 2300/0874* (2013.01); *B01L 2400/0487* (2013.01); *C12M 35/08* (2013.01)

(56) References Cited

U.S. PATENT DOCUMENTS

| | | |
|---|---|---|
| 2005/0260745 A1 | 11/2005 | Domansky et al. |
| 2006/0154361 A1 | 7/2006 | Wikswo |
| 2007/0122896 A1 | 5/2007 | Shuler et al. |
| 2007/0231880 A1 | 10/2007 | Chang-Yen et al. |
| 2008/0085556 A1 | 4/2008 | Graefing et al. |
| 2010/0099136 A1 | 4/2010 | Prabhakarpandian et al. |
| 2010/0159590 A1* | 6/2010 | Alley .................... C12M 29/10 435/374 |
| 2011/0183312 A1 | 7/2011 | Huang |
| 2011/0229961 A1* | 9/2011 | Higashi .................. C12M 23/16 435/287.1 |
| 2011/0250585 A1 | 10/2011 | Ingber et al. |
| 2013/0059322 A1* | 3/2013 | Hung .................... C12M 23/12 435/29 |
| 2014/0030752 A1* | 1/2014 | Cuiffi .................... C12M 23/44 435/29 |
| 2014/0113838 A1* | 4/2014 | Folch .................... C12M 23/12 506/10 |

* cited by examiner

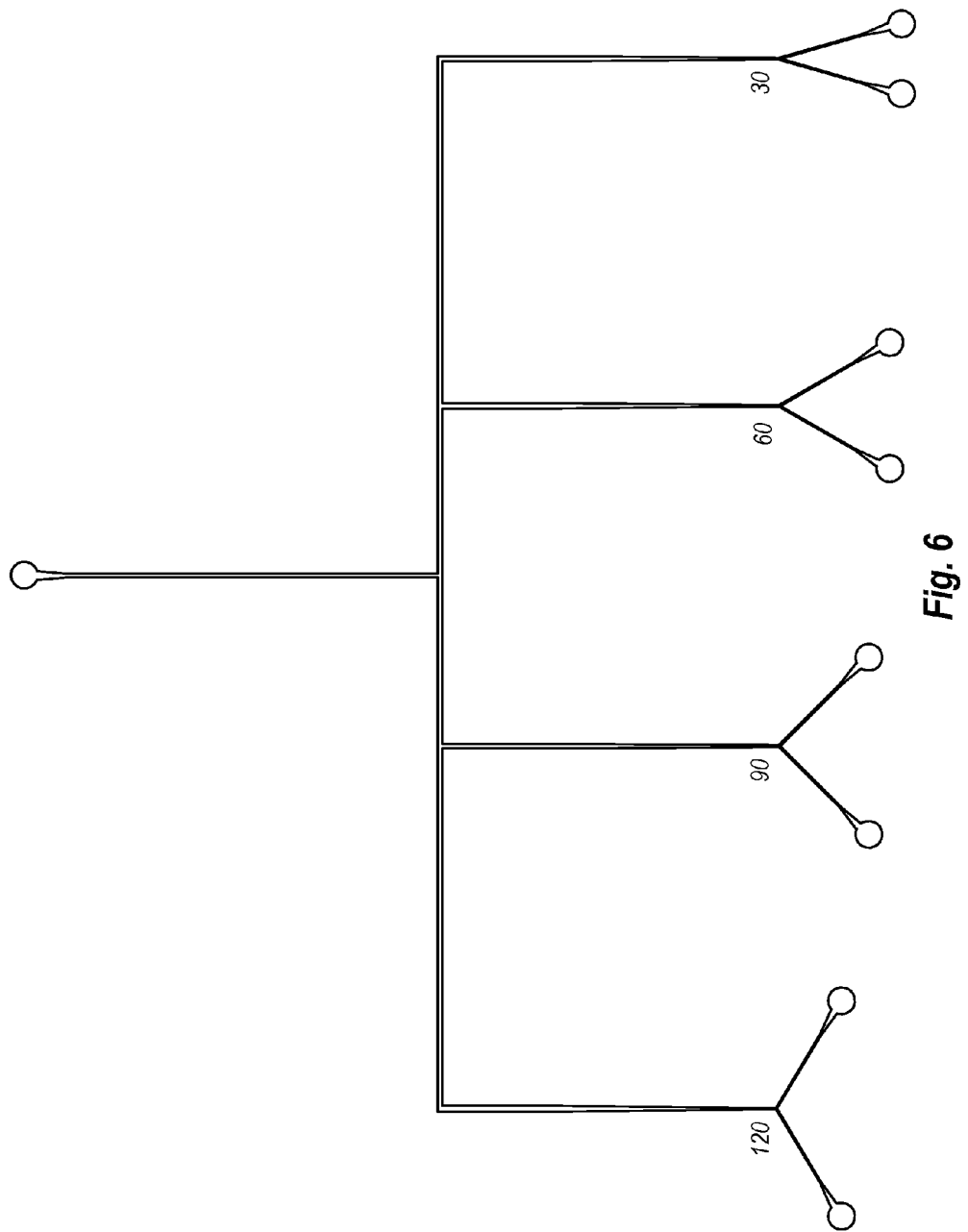

CELL CULTURE DEVICE WITH AN ARRAY OF MICROFLUIDIC NETWORKS

CROSS-REFERENCE

This patent application claims the benefit of U.S. Provisional Application No. 61/764,941 filed Feb. 14, 2013, and which is incorporated herein by specific reference in its entirety.

STATEMENT REGARDING FEDERALLY SPONSORED RESEARCH

This invention was made with Government support under SBIR Contract Number 1R43HL076034-01A1 awarded by the National Institutes of Health. The Government has certain rights to this invention.

BACKGROUND

There is a well-recognized need to develop high-throughput cell-based assays with increased physiological fidelity in order to be able to improve studies on the effects of therapeutic agents or therapeutic delivery systems on cell cultures.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 6 illustrates an embodiment of a microfluidic network comprising idealized bifurcations arranged in parallel.

Figure 1:
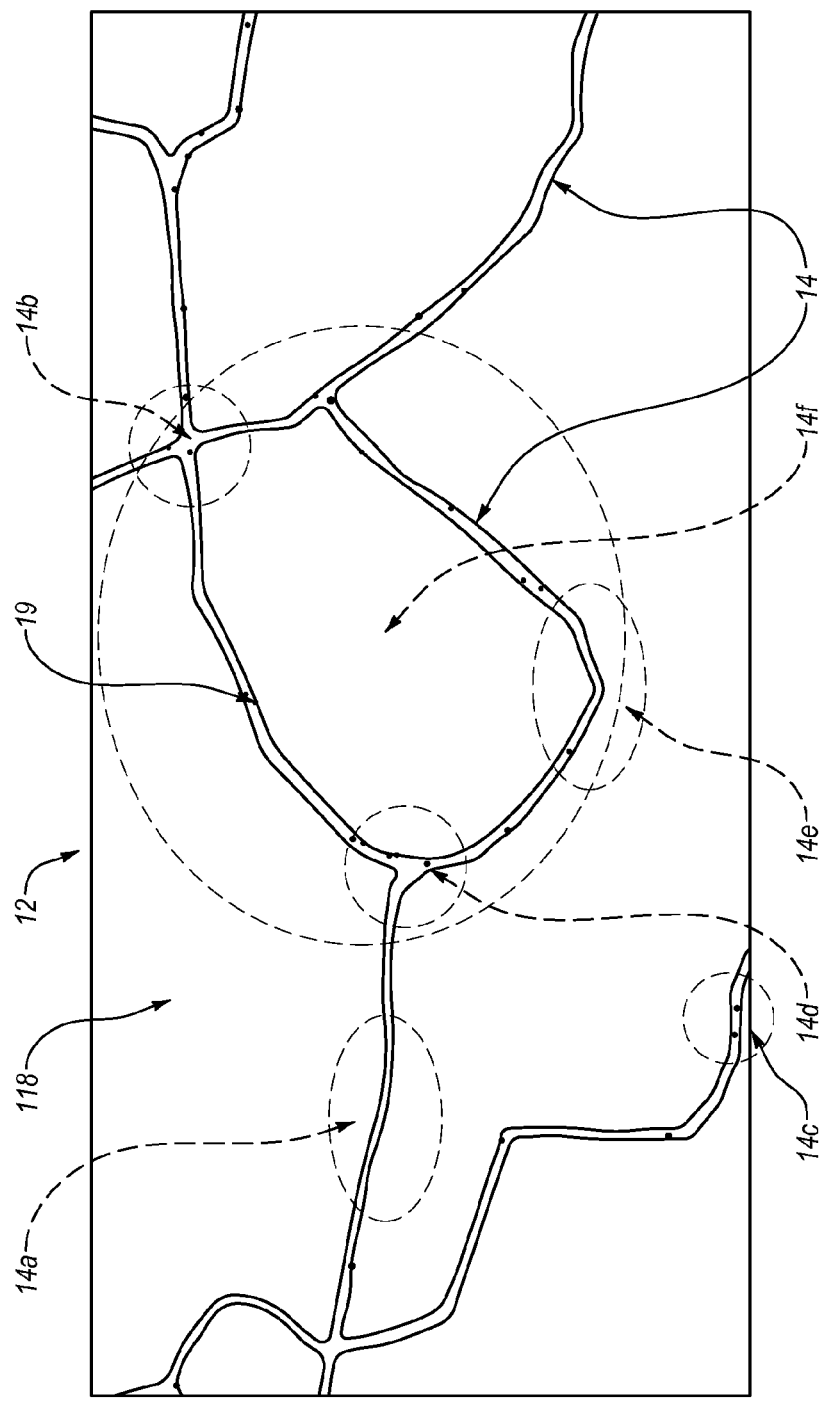
FIG. 1 illustrates an embodiment of a synthetic microvascular network in a microfluidic network.

All aspects of the embodiments described in the figures can be used in conjunction with other embodiments in other figures. While some aspects are shown to be symmetrical, those aspects may be asymmetrical.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to devices and methods involving arrays of two or more synthetic microvascular networks (SMNs) and/or idealized microvascular networks (IMNs). The devices and methods are useful for conducting a wide variety of assays, especially high-throughput cell-based assays for drug delivery, drug screening, drug toxicity, tumor metastasis, inflammation, thrombosis, and microvascular dysfunction, among others. The devices can be cell culture devices that have independent networks or linked networks. The devices can be cell culture devices with wells or assay regions with independent networks or linked networks that are linked to other networks in other wells or assay regions. As such, the cell culture devices can include multiple wells or assay regions that are independent or linked. The devices can also include fluid inlets and fluid outlets for each well or assay region and/or for each independent network and/or linked network. The wells or assay regions can have any configuration of cell culture features with vascular networks, tissue spaces, extravascular spaces, multi-chambered regions, or others described herein or known in the art.

The cell culture device can be used to study cell (e.g., leukocyte, platelets) or drug particle interaction with the vasculature and other extravascular regions. Particle adhesion to vascular endothelial cells is influenced by biochemical receptor-ligand interactions as well as vessel size and flow rate. The adhesion of particles including platelets, liposomes/lipisomes, and other microencapsulated drug carriers to microvascular endothelium is also influenced by the geometric features of the vasculature, and local hemodynamic factors such as wall shear stress, pressure, and residence time. Microvascular network geometries affected by metabolic syndrome, diabetes, and cancer are altered with respect to normal geometries. The altered geometries lead to altered flow profiles that may prevent, or be exploited to enhance, the efficacy of drugs used to treat these diseases.

The cell culture device can be made with microvascular network geometries capable of producing flow characteristics displayed by in vivo microfluidic networks. Consequently, it is possible to compare particle adhesion to vessels or extravascular spaces in healthy microvascular networks with particle adhesion in diseased microvascular networks.

U.S. Pat. No. 7,725,267, incorporated herein, discloses apparatus and methods that can be used to study fluid flow and particle adhesion in physiological vessels including arterioles, capillaries, and venules and combinations thereof, which can be included in the present invention. The apparatus and methods are useful for studying and optimizing drug delivery in the microvasculature. The apparatus includes microfluidic chips comprising synthetic microvascular networks (SMNs) with flow channels that possess key geometric and topological features that cause them to display fluid flow patterns and particle adhesion patterns found in physiological microvascular networks. The SMNs may be made using digitized images of physiological microvascular networks or averages of digitized images of physiological microvascular networks to generate templates for photolithography.

U.S. 2010/0227312, incorporated herein, discloses apparatus and methods useful for characterizing particle adhesion dynamics in biological microcirculation, which can be included in the present invention. The apparatus comprises microfluidic chips comprising combinations of idealized microvascular bifurcations and/or junctions or idealized microvascular networks comprising combinations of idealized bifurcations and junctions. The idealized microfluidic networks, junctions, and bifurcations consist of straight microfluidic channels joined at acute, right, or obtuse angles. Microfluidic chips containing combinations of idealized bifurcations and/or junctions having varying angles and parent/daughter channel asymmetries are able to predict at least some particle deposition patterns observed in SMNs.

U.S. Pat. No. 8,380,443, incorporated herein, discloses apparatus and method for an assay capable of identifying and screening for agents affecting the leukocyte adhesion cascade (LAC), which can be used with the present invention. The LAC assay device comprises an optically clear, plastic microfluidic chip comprising flow channels with diameters in the range of 10-500 µm. The luminal walls of the flow channels are coated with endothelial cells and the walls of at least a portion of the flow channels may contain 1-30 µm sized openings filled with a native or synthetic extracellular matrix that allow leukocyte migration into one or more tissue spaces. The flow channels may form idealized bifurcations or junctions, IMNs, or SMNs. The method and apparatus allow the assessment of individual steps in the LAC including rolling, adhesion, spreading, and extravasation of the leukocytes into the extravascular tissue space.

U.S. Pat. No. 8,355,876, incorporated herein, discloses methods and apparatus for screening tumor drug delivery vehicles, which can be included in the present invention. The apparatus includes a microfluidic device comprising an optically clear microfluidic chip containing a SMN or an IMN. The luminal surfaces of the flow channels are coated with a confluent layer of cultured endothelial cells. Tumor cells are cultured in an extravascular tissue space surrounded by flow channels comprising pores having dimensions in the range of 0.2-5 µm. The method assesses the ability of candidate drug delivery vehicles to reach and/or permeate cultured tumor cells and/or to transfect tumor cells, for example, may be used to discover and/or optimize the performance of drug delivery vehicles.

U.S. Pat. No. 8,417,465, incorporated herein, discloses a Synthetic Microvascular Blood-Brain Barrier (SyM-BBB) comprising a plastic, disposable and optically clear microfluidic chip with embedded microfluidic flow channels having geometric features and sizes similar to those found in vivo, which can be included in the present invention. The flow channels may form a SMN or an IMN. The SyM-BBB comprises an apical side in which endothelial cells are grown, and a basolateral side in which neuronal, glial, and astrocyte cells are grown or media conditioned with one or a combination of the cells. Fluid within channels on the apical side is in liquid communication with one or more basolateral side tissue spaces via 0.2-5 µm gaps in the walls.

The above-referenced U.S. patent and patent applications disclose microfluidic chips comprising SMNs, IMNs, and/or combinations of idealized bifurcations/junctions as well as assay methods employing such microfluidic chips, which can be incorporated into one or more of the microfluidic networks of the cell culture device described herein. The present invention discloses high-throughput devices and methods for performing assays on arrays of microfluidic chips comprising SMNs, IMNs, and/or combinations thereof as well as with or without idealized bifurcations/junctions. The device can be configured to provide for the control of multiple fluids through multiple fluid pathways (e.g., inlet pathways and outlet pathways into and out from individual wells or assay regions) and microfluidic network chip arrays of microfluidic chips and collection and processing of data from arrays of microfluidic network chip arrays.

This invention provides for devices and methods that combine two or more microfluidic networks including one or more of the SMN, IMN, and/or combinations of idealized bifurcations in a microfluidic chip array. One or more array plates can be used together with a microfluidic control system configured for performing a variety of high-throughput assays. The array plates can be configured as or configured for use in combination with open-bottom and sealed bottom microwell plates. A fully automated assay system can include the array plates having a plurality of microfluidic networks, means for pumping and controlling flows through the microfluidic networks to unique wells or assay regions, visual or other detection means for collecting data, and a data processor with software for analysis of collected data.

A "synthetic microvascular network" (SMN) is a man-made network comprising a plurality of interconnected, non-linear flow channels that form geometrical features and have fluid flow properties found in physiological microvascular networks. The flow channels in a SMN form an intersecting network that may be arranged to form synthetic analogs of an arteriole, capillary, venule sequence, with the flow channels varying in diameter from 2 µm to 500 µm. A flow channel in a SMN is non-linear and possesses one or more geometric characteristics of physiological microvascular vessels including variable cross-sectional shapes, variable cross-sectional areas, convolutions, turns, and inflection points. Two or more channels may form an anastomosis. A "convolution" is a tortuous irregularity caused by the infolding of a structure upon itself. A convolution in a microfluidic flow channel contains a path that doubles back upon itself between an inlet into the channel and an outlet from the channel such that a plot of the distance travelled along the channel vs. linear distance from the outlet comprises at least one portion with a positive slope. An "anastomosis" is formed when channels are connected in such a way as to provide more than one path for fluid to flow from a point in one channel to a point in another channel. Straight channels or other channels having non-physiological geometries may be used to link a synthetic microvascular network to other components of a microfluidic chip. These channels, however, are not a part of the microvascular network. A network of linear flow channels joining at angles, for example, is not a SMN.

As used herein, a microfluidic channel or flow path may have a rectangular, circular, semicircular, irregular or a combination of cross-sectional shapes. The dimensions of a channel are described, for example, by length, depth, and width wherein the depth is measured perpendicular to the plane of a microfluidic chip containing the channel, and length and width are measured in directions lying in the plane of the microfluidic chip containing the channel. Channels having circular or semicircular cross sections may be described as having variable depth and width relative to channels having rectangular cross sections or may alternatively be described in terms of channel diameter. Maximum depth and width when used to describe a channel having a circular or semicircular cross section are both equal to the maximum diameter of the channel. When used to describe a channel having a rectangular cross section, the maximum width and depth refer to the constant width and depth of a channel having a constant width and depth or to the highest values for width and depth for channels having variable width and depth.

A "microfluidic network" or "microfluidic chip" is constructed using techniques employed in the semiconductor industry such as photolithography, wet chemical etching, thin film deposition, laser patterning, and soft lithography using polymeric substrates. This is in contrast to microfluidic systems formed in gels made of proteins, chitosan, proteoglycans, and/or other extracellular matrix components. In general, a microfluidic chip is formed with a number of microchannels that are connected to a variety of reservoirs containing fluid materials. The fluid materials are driven or displaced within these microchannels throughout the chip using electrokinetic forces, pumps, and/or other driving mechanisms.

A "physiological" vascular network is a vascular network found in an animal or other organism and substantially possesses a geometry that is functional in the living organism in which it is contained. Most preferably, the animal is a living animal.

"Tortuosity" is a measure of the indirectness of a vessel or flow channel path. Tortuosity can be measured in several ways. One exemplary means of measuring tortuosity is to sum the angles between consecutive trios of points along the space curve represented by a vessel skeleton and then normalized by path length. Tortuosity may also be measured, for example, by counting inflection points along each vessel or flow channel and multiplying this number (plus one) times the total path length and then dividing by the distance between the ends of each vessel or flow path.

An idealized microvascular network (IMN) is a manmade network comprising interconnected flow channels that have certain fluid flow properties found in physiological microvascular networks. The diameters of the channels range from 10-500 µm and comprise of angles typically between 15° and 135°. One or more flow channels of an IMN may comprise porous walls such that liquid may move from the interior (lumen) of the flow channel into a space external to the lumen in a manner similar to the movement of fluid from the lumen of a physiological vessel into an interstitial space.

As used herein, the term "idealized" in association with a microfluidic network, junction, or bifurcation is used to describe a synthetic network, junction, or bifurcation consisting of straight microfluidic channels joined at acute, right, or obtuse angles.

The incorporated references describe idealized microvascular networks (IMN) and synthetic microvascular networks (SMN), which can be included in the inlets, outlets, or chambers therebetween. That is, an IMN can include one or more cell culture constructs (e.g., vascular network with one or more extravascular spaces) in an IMN configuration; or a SMN can include one or more cell culture constructs in a SMN configuration; or a hybrid IMN/SMN can include fluid pathways that include features of IMN and/or SMN and one or more cell culture constructs with the IMN or SMN configuration. Accordingly, the cell culture device can be configured with distinct chambers that are modeled by IMN and/or SMN. Some configurations can include only IMN chambers, some may include only SMN chambers, and some can include a combination of both IMN and SMN chambers. The cell culture device can be configured for any organ or biological organ pathway with an appropriate network construct simulating an organ where the simulated organs can be studied alone or in combination with other organs in a biological organ pathway. For example, the cell culture device can simulate the liver, kidney, heart, lung, brain, stomach, intestine, blood brain barrier, vascular networks, or others. As such, the distinct chambers in the network constructs can have unique cell cultures that are indicative of the different cell types or tissue types of the different layers and central region of an organ. A single embodiment of the cell culture device can be configured to be different organs by the different cells or cell combinations that are present in the distinct cell cultures of the distinct chambers of an independent network or for linked networks. That is, different types of cells and cell combinations can distinguish a network construct simulating the heart from a network construct simulating the liver, where without the cells the network constructs can appear similar or identical.

Obtaining Geometries of Physiological Vascular Networks

A complete map of a vascular network is constructed from one or more images of a physiological vascular network, such as a group of recorded fluorescent images. The network map is then digitized by tracing the path of each vessel on the assembled group in an AutoCad Map® using a computerized drawing board such as Drawing Board III® or Cal-Comp. Fluorescent images may also be digitized from videotape using a frame grabber and assembled online into a digitized collage representative of the microvascular network.

After a network is digitized, an AutoCad Map® cleanup routine may be used to ensure that all vessels are properly connected at their common nodes. A tolerance value is set, which distinguishes between common nodes and neighboring end points. Each vessel is graphically represented by a polyline consisting of a series of straight lines connected through vertices. The system compares the distance between successive vertices in a polyline to the set tolerance value. The vortex is removed from the polyline if the distance is below the set tolerance value. Images of physiological microvascular networks for use in obtaining geometries may also be obtained using digital photography (e.g., retinal imaging).

To reduce error resulting from the manual tracing of networks from composite images, an automated tracing system such as ENVI® (RSI Research Systems, Inc.) can be used and the traced images can then be directly incorporated into and interfaced with databases in Autocad Map®.

Obtaining Reconstructed "Averaged" Vascular Networks

"Averaged" or reconstructed vascular networks have geometries constructed from the digitized geometries of at least two actual microvascular networks and can be used, for example, to translate a three-dimensional vascular or microvascular network into a two-dimensional vascular or microvascular network. The images are analyzed as described above and subjected to a morphological analysis to obtain statistical data of morphometric parameters including ratios of parent-to-daughter vessel diameters, branching angles, distances between branches, ratios of branch length to branch channel diameter, tortuosity, bifurcation branch density, and recombining branch density. An averaged vascular and/or microvascular network is generated using averaged morphometric data and/or stochastic sampling of probability density functions for morphometric data. An averaged vascular and/or microvascular network may be generated using values selected from a variety of statistical distributions for individual morphometric parameters. The values used need not be "average," "mean," or "median" values for measured morphometric parameters.

It is also possible to construct hypothetical SMNs without the use of digitized images from physiological microvascular networks. For example, one may draw a hypothetical microvascular network having a physiologically realistic geometry. The drawing may be created in digital form using a computer or on paper and converted into digital form. One may also wish to manually modify a digitized physiological network to introduce and/or remove one or more geometric features for the purpose of assessing the influence of the feature(s) on, for example, flow properties and/or particle adhesion in the network. A series of SMNs representing different stages of angiogenesis may be useful for studying, for example, drug and/or nutrient delivery to solid tumors or healing tissue. The flow channel geometries used may be derived from images taken at time intervals of actual angiogenesis in an animal, computer programs that model angiogenesis processes, or hypothetical SMNs.

Microfluidic Chip Manufacture

Microvascular network structures obtained from in vivo animal data or averaged microvascular networks are patterned onto an optically clear plastic such as PDMS (polydimethylsiloxane) using conventional soft lithography/replica casting techniques and as described in U.S. Pat. No. 7,725,267 and which is incorporated herein by reference. Each network structure can be contained within a well or assay region A microfluidic chip comprising one or more SMNs is preferably made from polydimethylsiloxane (PDMS) using polymeric microfluidic technology but may also be made using any one of a variety of techniques commonly used in semiconductor or microfluidic technologies. PDMS microfluidic chips having a thickness of as little as 100 µm and less can be used for long-term cell culture and cellular assays. By bonding the polymer microchannel onto a glass bottom laid out in a desired form, microfluidic chips may be formed onto standard 24 or 96 well plates, for example, for high-throughput screening.

Microfluidic Chips Comprising a SMN

FIG. 1 is an image of a selected portion of a simple synthetic microvascular chip. A plurality of interconnected, nonlinear flow channels 14 form the visible portion of a synthetic microvascular network (SMN) 12, which are visible within a plastic substrate 18. The nonlinear flow channels 14 in this example have a rectangular cross-sectional shape and comprise curves, inflection points, and variable cross-sectional areas. The flow channels form junctions, intersections, and an anastomosis. Fluorescent particles 19 are visible moving through the SMN. The SMN is shown to have nonlinear flow channels 14 with variable cross-sectional area 14a, intersections 14b, inflection points 14c, junctions 14d, curves 14e, and anastomosis 14f.

Figure 2A:
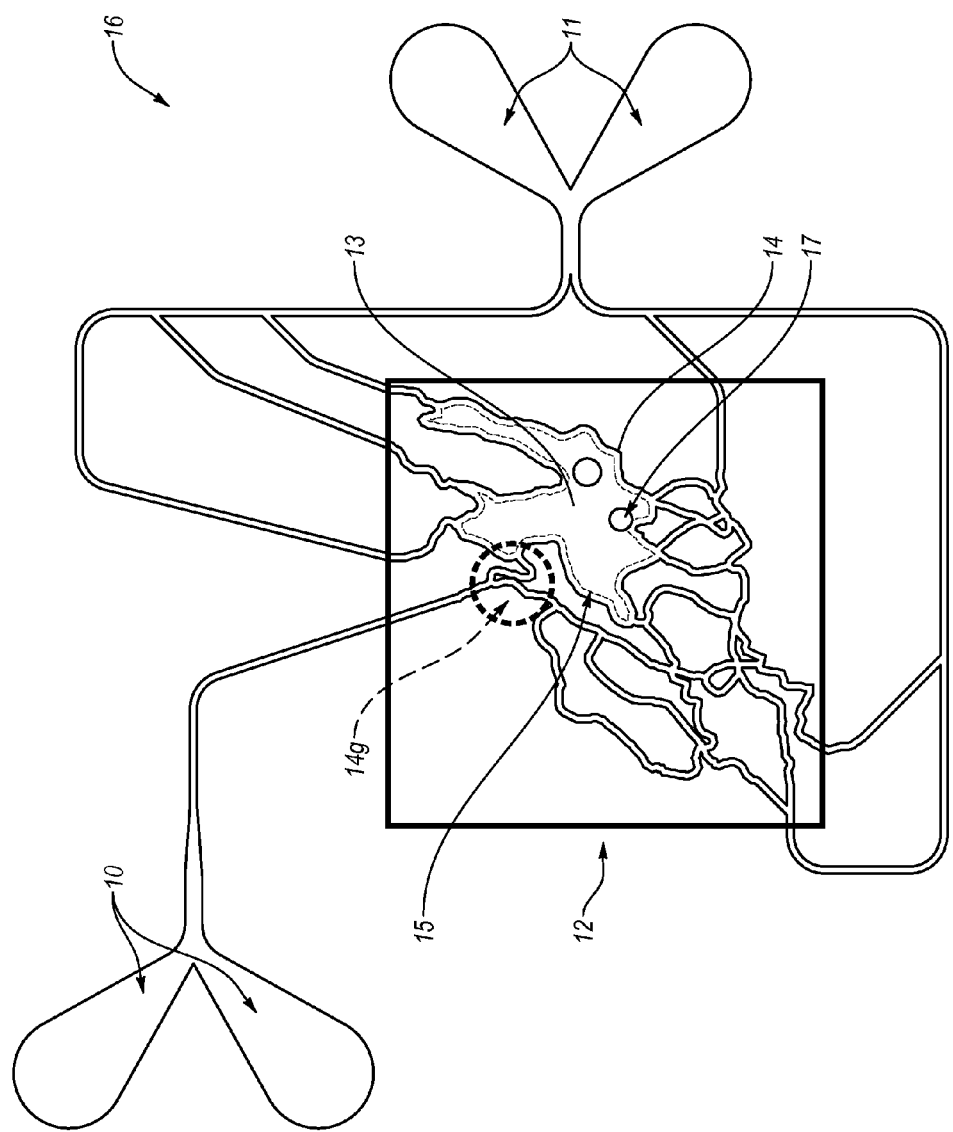
FIGS. 2A and 2B illustrate an embodiment of a SMN comprising an extravascular tissue space.

A microfluidic chip comprising the synthetic microvascular network (SMN) 12 and a tissue space 13 is illustrated in FIG. 2A. The SMN 12 comprises a plurality of interconnected, nonlinear flow channels 14, in fluid communication with an inlet port 10 and an outlet port 11. In addition to the geometric features visible in FIG. 1, a flow channel comprising a convolution 14g is visible in FIG. 2A. The inlet port 10 and the outlet port 11 each have two lobes in this embodiment to facilitate easy connections to reservoirs and the inlet and outlet ports may have single lobes and/or other shapes as well. This embodiment shown has one inlet port 10 and one outlet port 11. Other embodiments may have more than one inlet and/or outlet. The SMN shown comprises an extravascular tissue space 13 that is separated from and in fluid contact with at least one nonlinear flow channel 14 of the SMN 12 via gaps or pores 15 having cross-sectional dimensions of between 0.2 and 30 µm. The cross-sectional dimension is, for example, a diameter in the case of circular pores and the length of the longest side for rectangular gaps. The extravascular tissue space separated from the lumen of one or more flow channels by porous walls allows liquid to diffuse from the flow channels into the tissue space. The tissue space 13 preferably has cross-sectional luminal dimensions of between 100 µm and 1 cm. The extravascular tissue space 13 preferably comprises one or more ports 16, 17 that may serve as a fluid inlet and a fluid outlet for the lumen of the tissue space or may serve, for example, as a combined inlet/outlet and a pressure port for applying variable pressure to the lumen of the tissue space 13. The embodiment illustrated in FIG. 2A has one tissue space 13. Other embodiments may have more than one tissue space. The ports 16, 17 can be coupled to a fluid transport network, such as one that includes a manifold and unique flow channels for each inlet port and outlet port.

Figure 2B:
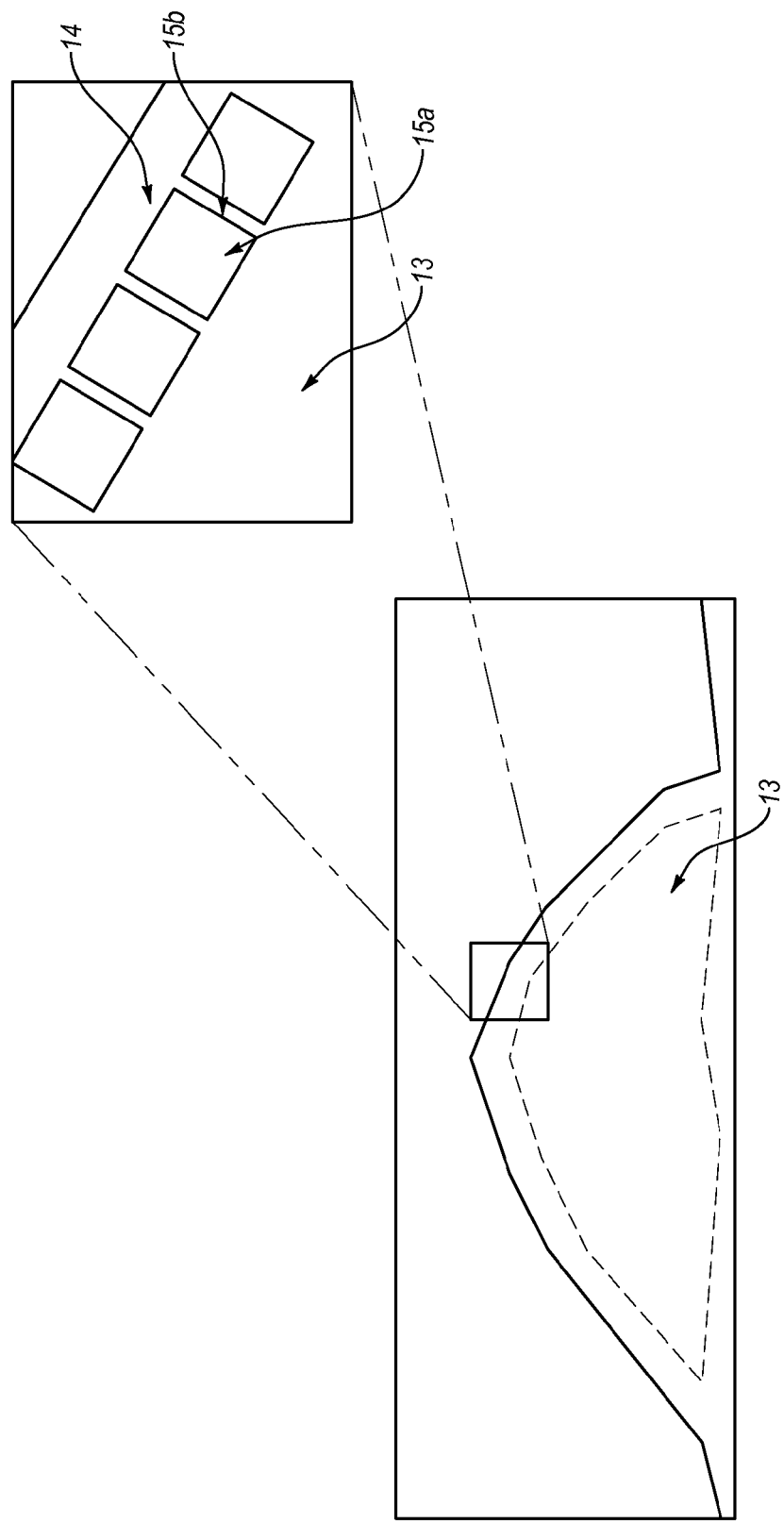
Figure 8:
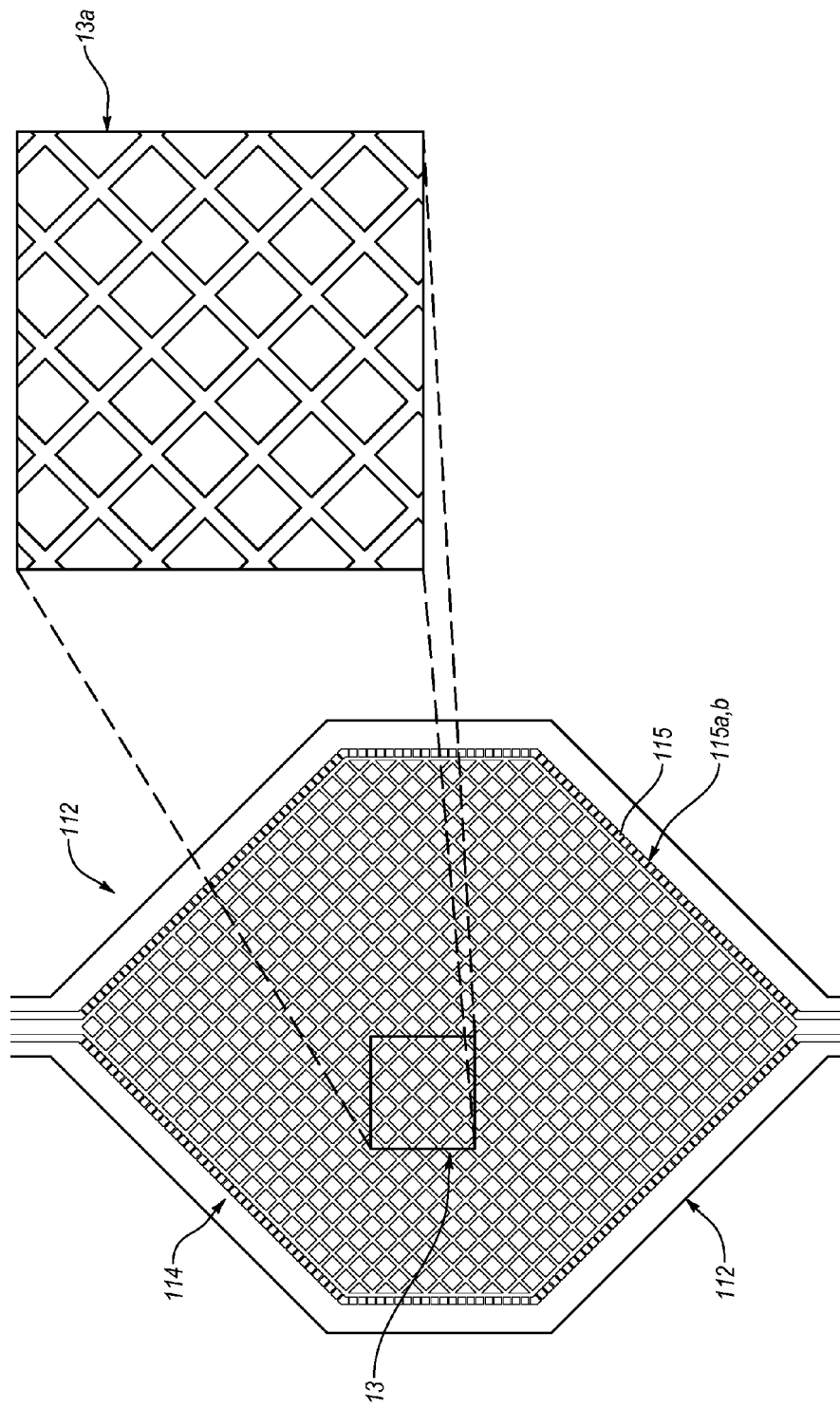
FIG. 8 illustrates an embodiment of an idealized microfluidic network comprising an extravascular tissue space that contains posts.

One embodiment of a wall of a flow channel separating the flow channel lumen from the lumen of the tissue space 13 is shown in detail in FIG. 2B. In this embodiment, one wall of the nonlinear flow channel 14 is constructed such that portions of the wall contain gaps 15b located between portions of the wall, called islands 15a, which may be configured to provide gaps 15b of various selected sizes. For fabrication of the SMN 12 comprising the extravascular (extra-flow channel) tissue space 13, CAD drawings of a physiological network are modified to include gaps 15b with desired gaps or pores in the walls of the vessels. The patterns of these vessels include tissue sections comprising a portion of or the entire physiological tissue space. The lumens of the tissue spaces shown in FIGS. 2A and 2B may comprise posts, pillars, or other structures made of plastic substrate to facilitate the growth of adhesion-dependent cells such epithelial cells, fibroblasts, bone marrow cells, embryonic cells, hepatocytes, myocytes, neural cells, adipocytes, brain cells, liver cells, heart cells, kidney cells, lung cells, stomach cells, intestine cells, pancreas cells, ovary cells, cervix cells, spleen cells, artery cells, venule cells, capillary cells, connective tissue cells, organ tissue boundary layer cells, connective tissue cells, muscle cells, bone cells, nervous tissue cells, germ cells, stem cells, tumor cells, cultures thereof, 3-D tissues thereof, or any cell of any type from any organism, and combinations thereof. Also, these features can be included in the tissue space 13 as shown in FIG. 8.

Microfluidic Chips Comprising Idealized Bifurcations or an IMN

Figure 3A:
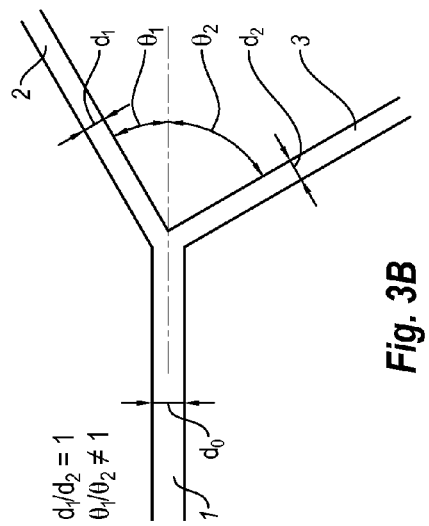
FIGS. 3A-3D illustrate embodiments of idealized bifurcations.

The simplest component of an idealized microfluidic network is a single idealized junction or bifurcation in which fluid flow converges or diverges, respectively. FIG. 3A shows the basic elements of an idealized bifurcation having an inlet leading into parent channel 1 and two daughter channels 2, 3 of equal diameters or cross section that diverge from the line of the parent channel in a symmetrical manner and leading to two outlets. The same structure with reversed flow having two inlets and one outlet would form an equivalent junction.

The idealized bifurcations and junctions in an idealized microfluidic network consist of linear parent and daughter channels having rectangular or circular or semicircular cross sections that diverge or converge at angles of between 15° and 135°. The diameters or cross sections of the channels are between 10 and 500 µm. The bifurcations and junctions are categorized as illustrated in FIGS. 3A-3D. In these figures, $d_0$, $d_1$, and $d_2$ represent the diameters of the parent and first and second daughter channels, respectively. The $\theta_1$ and $\theta_2$ represent the angles formed between the parent channel and the first and second daughter channels, respectively.

Figure 3B:
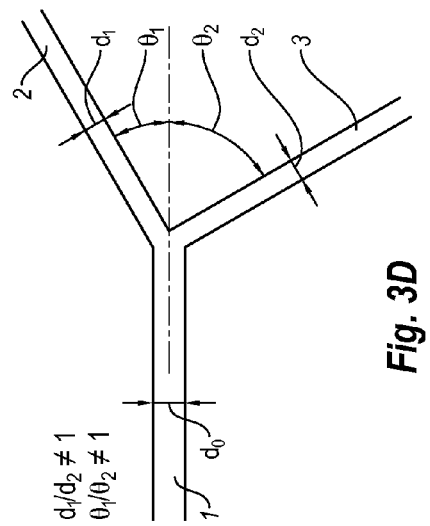
Figure 3C:
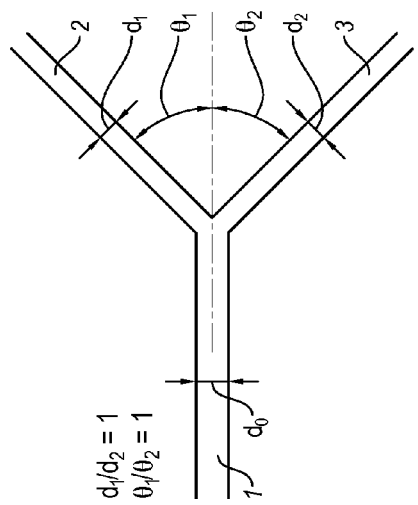
Figure 3D:
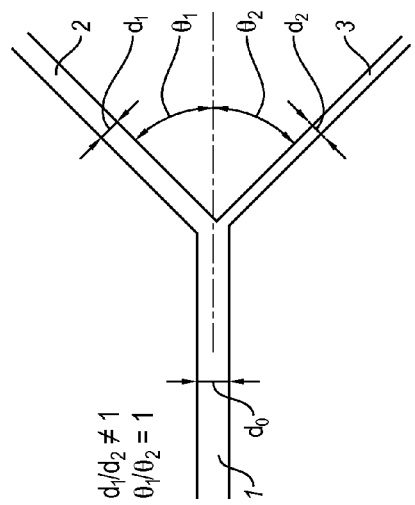

FIG. 3A shows the structure of a symmetric bifurcation with symmetric daughter diameters. In this case, the parent branch 1 splits into two daughter branches 2 and 3 such that the diameter of daughter 2 is the same as the diameter of daughter 3. The angle between the parent 1 and daughter 2 is identical to the angle between parent 1 and daughter 3. FIG. 3B shows the structure of an asymmetric bifurcation with symmetric daughter cross-sectional areas (width×depth for channels having a rectangular cross section, and diameter×π for channels having circular cross sections, and diameter/2×π for channels having semicircular cross sections). In this case, the parent branch 1 splits into two daughter branches 2 and 3 such that the diameter of daughter 2 is the same as the diameter of daughter 3. The angle between the parent 1 and daughter 2 is different from the angle between parent 1 and daughter 3. FIG. 3C shows the structure of a symmetric bifurcation with asymmetric daughter diameters. In this case, the parent branch 1 splits into two daughter branches 2 and 3 such that the diameter of daughter 2 is different from the diameter of daughter 3. The angle between the parent 1 and daughter 2 is identical to the angle parent 1 and daughter 3. FIG. 3D shows the structure of an asymmetric bifurcation with asymmetric daughter diameters. In this case, the parent branch 1 splits into two daughter branches 2 and 3 such that the diameter of daughter 2 is different from the diameter of daughter 3 and the angle between the parent 1 and daughter 2 is different from the angle parent 1 and daughter 3.

Figure 4:
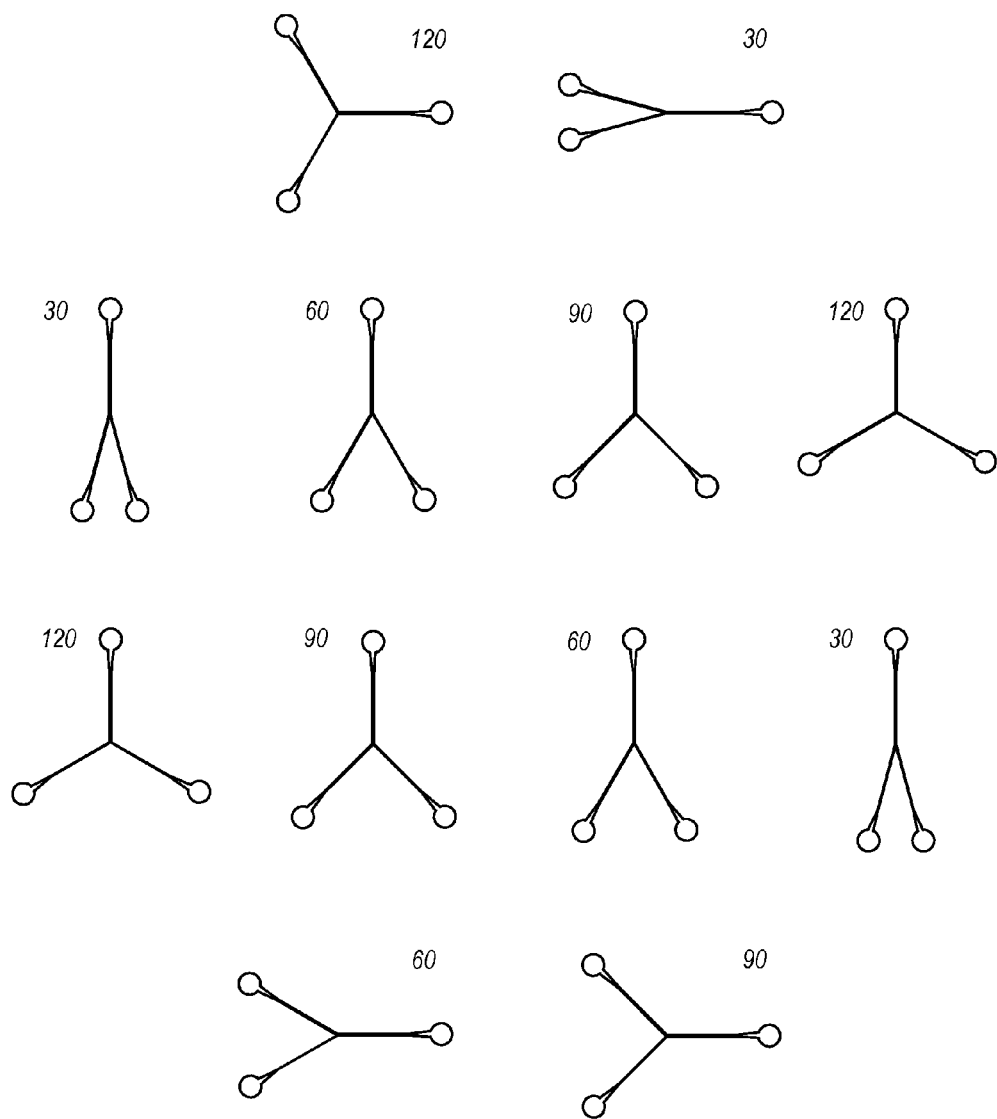
FIG. 4 illustrates different types of symmetric idealized bifurcations.
Figure 5:
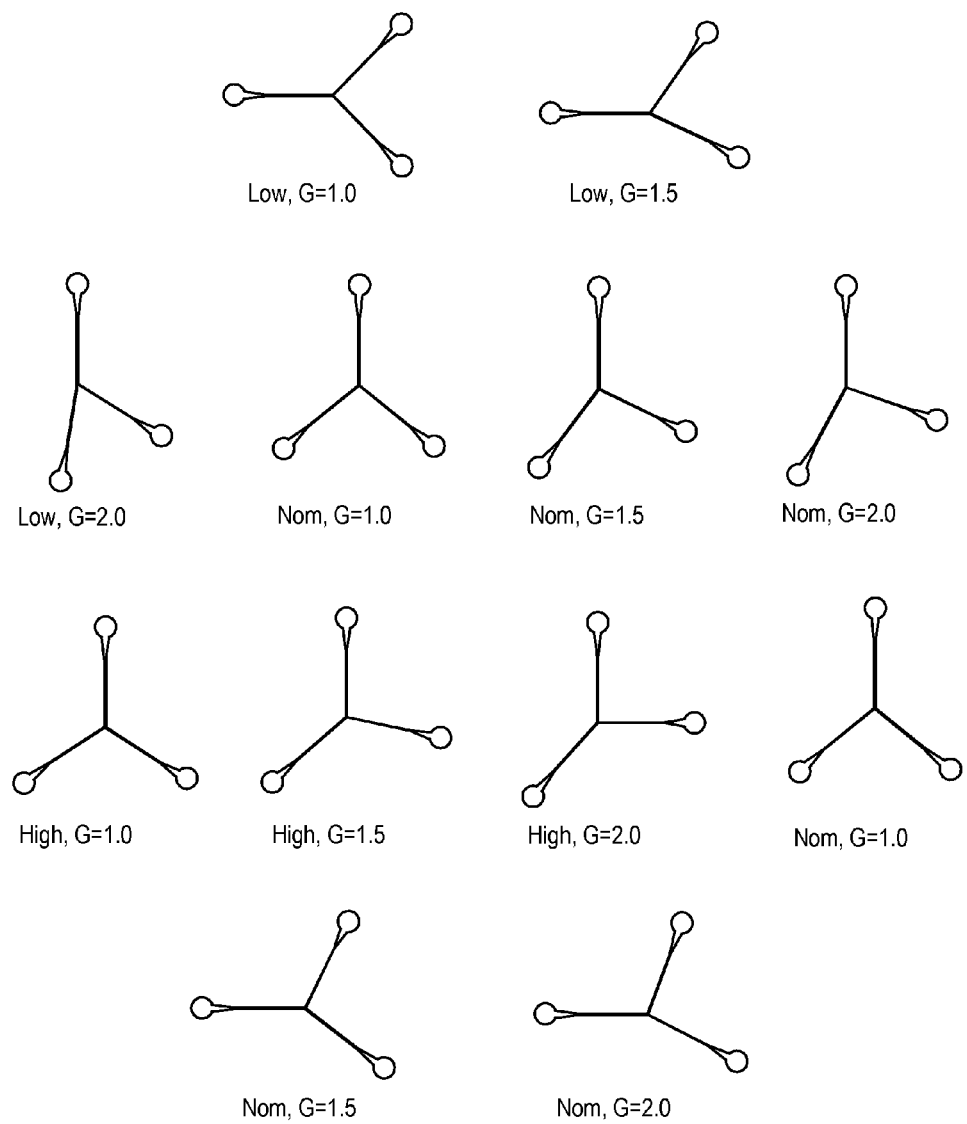
FIG. 5 illustrates different types of asymmetric idealized bifurcations.

A microfluidic chip contained in an array may comprise a single idealized bifurcation or junction or, more preferably, a plurality of junctions and/or bifurcations arranged in parallel and/or series. FIG. 4 and FIG. 5 illustrate single microfluidic chips, each comprising a plurality of microfluidic bifurcations/junctions arranged for simultaneous use or in a serial fashion, one after another. FIG. 4 shows a microfluidic chip comprising a plurality of symmetric bifurcations with different contained angles (shown as 30°, 60°, 90°, and 120°) used sequentially to implement a particle adhesion assay. FIG. 5 shows a microfluidic chip comprising a plurality of asymmetric bifurcations with Low, Nom (nominal), and High contained angles, wherein Low refers to the smallest contained angle, and High refers to the largest contained angle. The degree of angle asymmetry is indicated by G=1, G=1.5, and G=2.0, where increasing G values indicate increasing asymmetry in the bifurcation and the bifurcations may be used sequentially, for example, to perform a particle and/or cellular adhesion assay. Open circles in FIGS. 4 and 5 indicate inlets or outlets, depending on the direction of flow though the bifurcations. The inlets/outlets are preferably in fluid contact with inlet and outlet manifolds and pumping means. To avoid connecting the numerous inlets and outlets shown in FIG. 4 and FIG. 5 to an inlet manifold and an outlet manifold, some or all of the inlets and/or outlets may be linked to a single inlet and/or outlet port in the microfluidic chip (FIG. 2A). The inlet and/or outlet port, in turn, is in fluid communication with an inlet and/or outlet flow paths and/or manifold (see FIG. 10). FIG. 6 illustrates a single microfluidic chip comprising a plurality of bifurcations arranged in parallel, where the entirety of the network can be in a single well or assay region, or the bifurcations can be at unique wells or assay regions in a cell culture assay plate. The angle of bifurcation (30°, 60°, 90°, 120°) in the X-Y plane of the microfluidic chip is shown for each bifurcation.

Figure 7A:
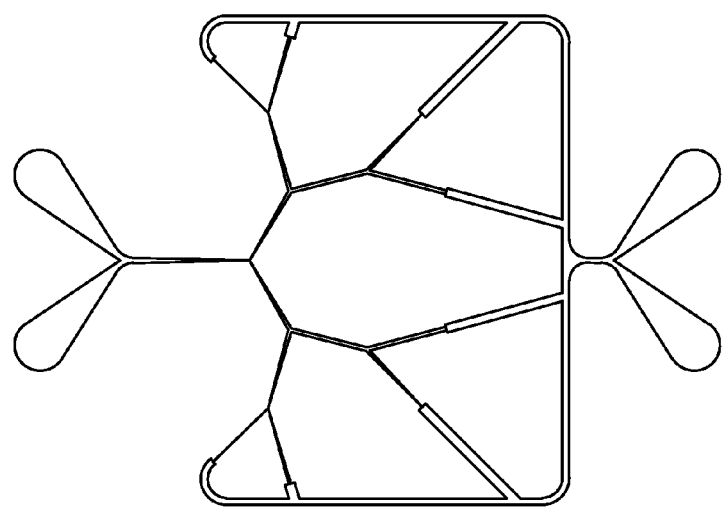
FIGS. 7A-7C illustrate geometries of three embodiments of idealized microfluidic networks.
Figure 7B:
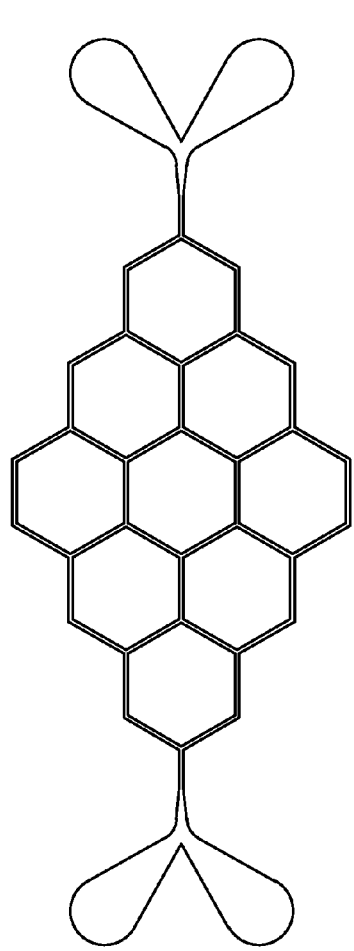
Figure 7C:
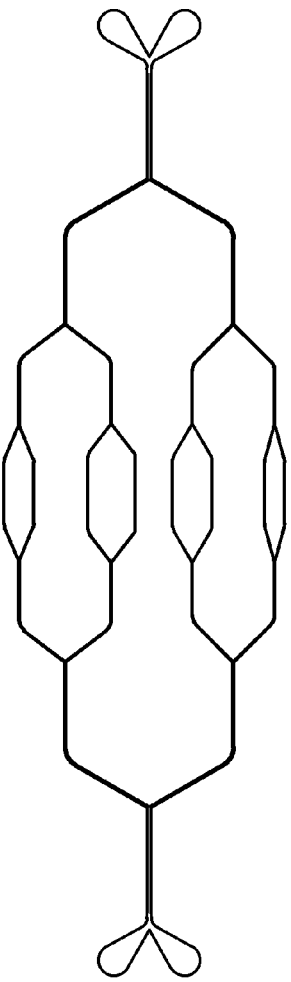

An IMN or IMN/SMN array may also employ a plurality of idealized bifurcations and junctions arranged to form an idealized microfluidic network. FIG. 7A illustrates the geometry of channels in a single microfluidic chip comprising a plurality of bifurcations in which no contained angle is repeated and the lengths of the individual branches are maintained constant throughout the network. FIG. 7B illustrates the geometry of channels in an idealized microfluidic network comprising a plurality of identical, symmetric bifurcations and junctions. FIG. 7C illustrates the geometry of channels in an idealized microfluidic network comprising a plurality of bifurcations and junctions in which no bifurcation or junction geometry is repeated. An IMN may additionally or alternatively comprise one or a plurality of junctions/bifurcations with more than three channels, such as junctions/bifurcations having one parent and three daughter channels, for example. The individual structures of FIGS. 7A-7C can be individual wells or assay regions, or distributed across multiple wells or assay regions with features within the well or assay regions and the flow paths connecting the wells or assay regions.

FIG. 8 shows a portion of an IMN 112 in a microfluidic chip. The IMN 112 comprises the idealized extravascular tissue space 13 surrounded by linear flow channels 114. Walls 115 separating the tissue space 13 from the linear flow channels 114 are permeable to aqueous buffers and are formed by plastic structures 115*b* separated by gaps 115*a* that range in size from 0.2 µm to 5 µm. Alternatively, the walls 115 may be made liquid permeable by way of pores in the wall that are from 0.2 µm to 30 µm in diameter. The extravascular tissue space 13 contains posts 13*a* (e.g., pillars) configured to facilitate the growth of adhesion-dependent cells to form a three-dimensional solid mono- or co-tissue culture or tumor. The posts 13*a* can be included in any vascular fluid flow path or extravascular space in any of the microfluidic chips. The posts 13a distribution, amount or arrangement or shape.

While the microfluidic chips and microvascular networks in a microfluidic chip array are largely planar, the depth of tissue spaces and the inclusion and arrangement of posts or other scaffolds within the tissue spaces can be designed to produce tumor cell monolayers and bilayers, as well as three-dimensional solid tumors or tumor and/or non-tumor cell co-cultures. A tissue space may, therefore, be constructed to have a larger depth than the surrounding flow channels in the microfluidic chip. The location of each tissue space in the network may be selected by the user. For SMN extravascular tissue spaces, tissue spaces defined by images from one or more physiological networks may be selected for the location of a SMN tissue space or as an area of solid chip substrate.

Figure 9:
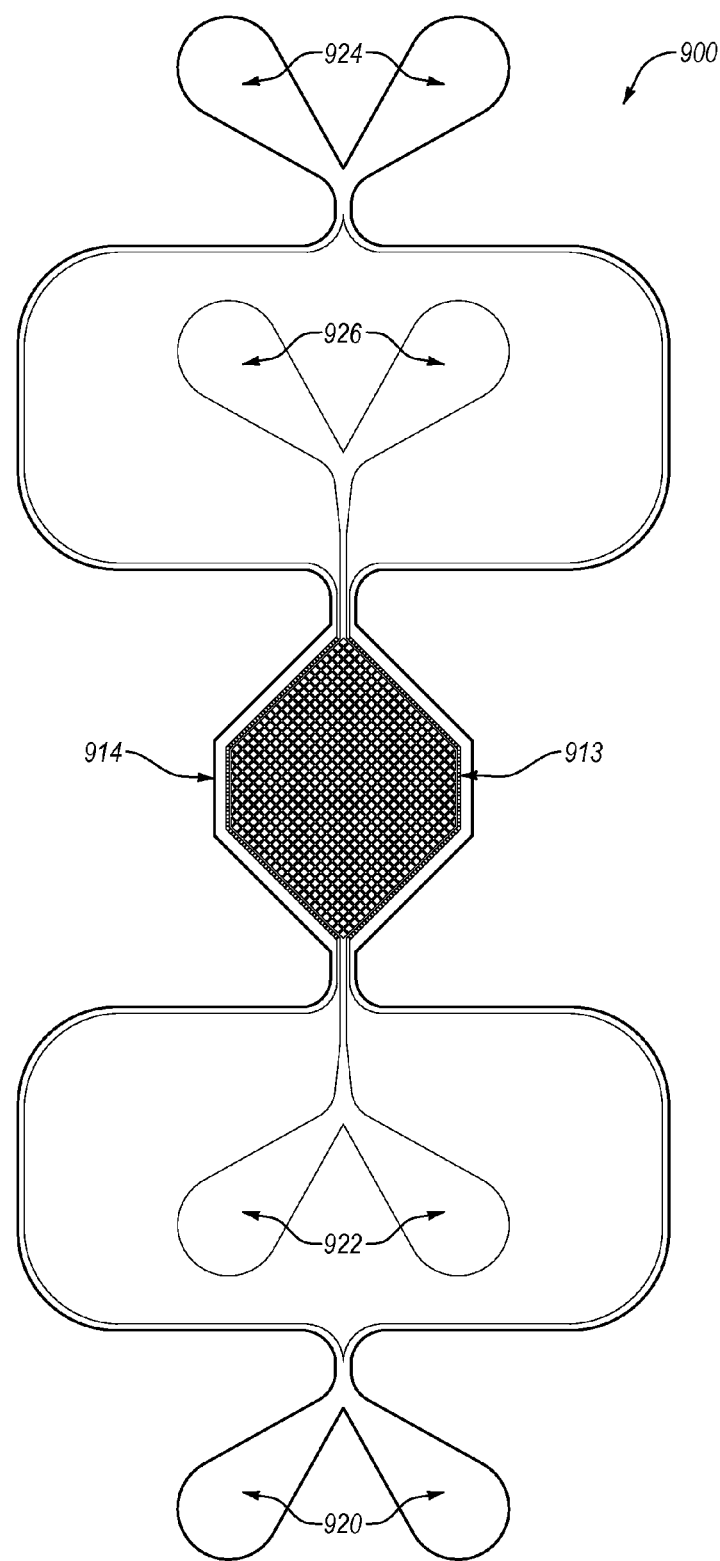
FIG. 9 illustrates an embodiment of a layout of a microfluidic network comprising an idealized microfluidic network and an idealized extravascular tissue space that contains posts.

FIG. 9 shows an example of an IMN 900 with a vascular pathway 914 surrounding a tissue space 913 containing posts (see FIG. 8) that, for example, serve as anchors to facilitate the formation of a three-dimensional tumor. The vascular pathway 914 and the tissue space 913 are each in fluid communication with a fluid inlet (e.g., vascular inlet 920 and tissue space inlet 922) and a fluid outlet (e.g., vascular outlet 924 and tissue space outlet 926). Separate inlets and outlets for the vascular pathway 914 and the tissue space 913 allow fluid to be pumped through both the vascular pathway 914 and the tissue space 913. Fluid flows through the vascular inlet 920, and the vascular outlet 924 of the vascular pathway 914 can be controlled to maintain specified flow rates and shear rates, for example. Fluid flow and/or pressure applied through the tissue space inlet 922 and the tissue space outlet 926 of the tissue space 913 may be controlled to maintain a simulated interstitial pressure or to simulate lymphatic drainage. The entirety of the elements in FIG. 9 can be included in a single well or assay region with the inlets and outlets fluidly coupled to different fluid pathways of the manifold. Alternatively, each of the elements of FIG. 9 may be in separate wells or assay regions with the fluid paths connecting the separate wells or assay regions (see FIGS. 10A and 10B).

The examples shown in FIGS. 8 and 9 illustrate IMNs on microfluidic chips that contain one or more extravascular tissue spaces and, optionally, posts within the tissue spaces. Extravascular tissue spaces with or without posts may also be included in SMNs, as indicated in the description of FIG. 2A.

Cell Cultures in SMNs, IMNs, and Bifurcations

The channels forming SMNs, IMNs, bifurcations, and the luminal surfaces of tissue spaces may be coated with native or recombinant proteins, glycoproteins, proteoglycans, or other substrate molecules to assay for associations with particles or to facilitate the growth of cells on the inner surfaces of the channels. Examples of substrate molecules include collagen, gelatin, laminin, and fibronectin. Other materials such as matrigel, puramatrix, alginate beads, or others that can be used, such as a monolayer substrate or a 3-D gel can be used. The channels may also be coated with adhesion molecules such as P-selectin, E-selectin, ICAM-1, or other receptors to facilitate adhesion of specific cell types or particles such as lipisomes or drug encapsulating or targeting agents.

Channels forming SMNs, IMNs, bifurcations, and the luminal surfaces of tissue spaces may be coated with cultured cells, which may be selected from primary cultures of freshly harvested cells and immortalized cell lines such as transformed and cancer cell lines and neural cell lines. Channels may be coated with a single cell culture or a co-culture comprising two or more cell types. Preferably, the flow channels are coated with endothelial cells. Examples of specific endothelial cell types that may be cultured within a SMN include human microvascular endothelial cells (HMECs), human umbilical cord vascular endothelial cells (HUVECs), and bovine aortic endothelial cells (BAECs). Non-adherent cells or cells in suspension including blood cells (WBC/RBC, platelets), tumor cells, or stem cells may also be circulated through the flow channels. A tissue space may contain cultured cells and/or a first type of tumor cells. One or more of endothelial cells, epithelial cells, fibroblasts, bone marrow cells, embryonic cells, hepatocytes, myocytes, neural cells, adipocytes, and a second type of cultured tumor cells may be contained in a tissue space in addition to cultured cells and/or tumor cells in the tissue space. Additionally or alternatively, a chemoattractant, an extracellular matrix, a basement membrane, a synthetic matrix, natural occurring matrix, a cytokine, a cytokine-secreting cell, a gel, a cell culture, or a source of a leukocyte chemoattractant, may also be contained in a tissue space in addition to cultured cells and/or tumor cells in the tissue space.

Additional Microfluidic Chip Components

Microfluidic chips generally comprise reservoirs in fluid communication with network inlets/outlets, inlet/outlet ports, and/or bifurcations. Reservoirs may contain, for example, buffers, solutions for coating flow channels/tissue spaces with desired matrices and/or cells, cell media, test samples, waste, or wash buffer. One or more reservoirs may be dedicated to an individual microfluidic network or group networks or bifurcations. Typically, more than one reservoir is available for each network or bifurcation to provide sources for multiple reagent fluids. The contents of each reservoir may be supplied through connections to a fluidic manifold that is connected to an array of microfluidic chips. Fluids may be pumped through a network, bifurcation, or microfluidic chip in a single pass or recirculating manner. Pumping means, such as one or more dielectrophoretic pumps, may be located within a microfluidic chip and may be configured for pumping fluid through all or a portion of the microfluidic chip, mixing fluids, or cleaning microfluidic components. One or more fluidic arms configured to withdraw a desired volume of solution from a reservoir and inject the precise volume into a microfluidic chip may be used to convey fluid from one or more reservoirs to each chip. Valves may be located between reservoirs and microfluidic network or bifurcation inlets to control and/or select fluid flow from one or more reservoirs. Valves may also be included to restrict flow in certain channels of SMN or IMN. These components and functionalities can be employed with the embodiments illustrated in FIGS. 10A and 10B.

Devices with a Plurality of Microfluidic Networks

Figure 10A:
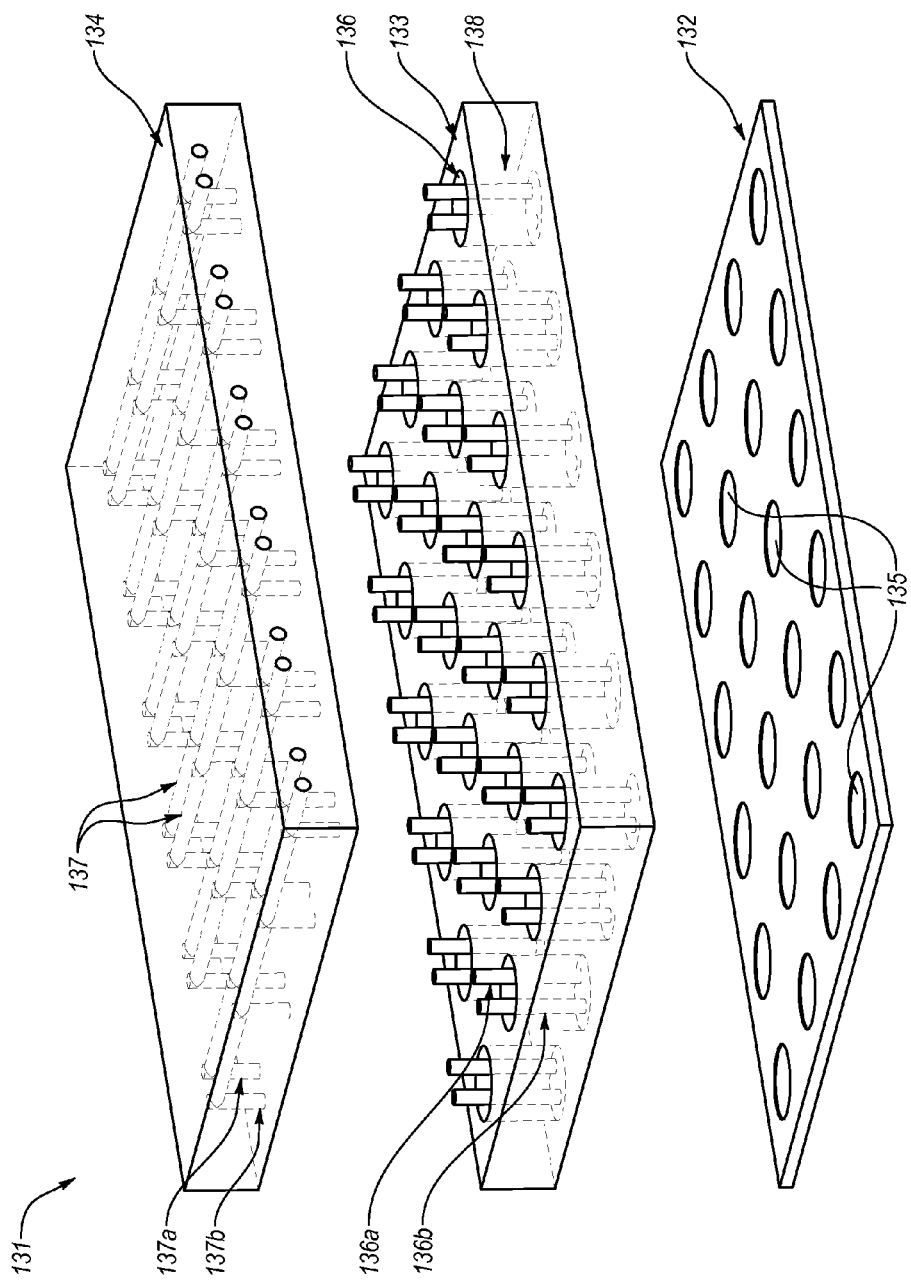
FIGS. 10A and 10B illustrate embodiments of microfluidic devices having an array of microfluidic networks, each spot or block being a distinct microfluidic network.
Figure 10B:
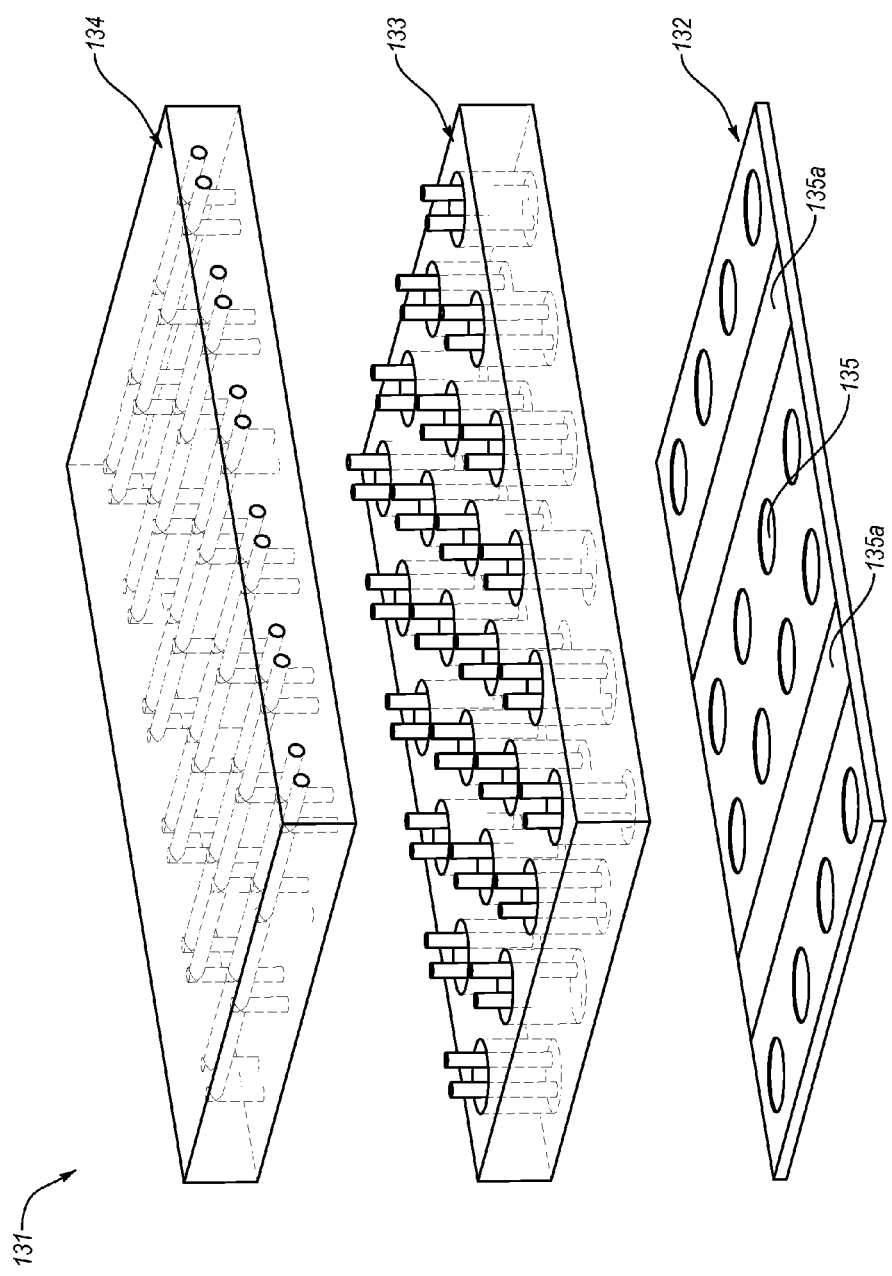

The footprint of a microfluidic chip comprising a SMN, an IMN, and/or a bifurcation may be sized between 1 mm and 5 mm to fit inside a well of a micro-well plate. In such cases, an array of the microfluidic chips may be affixed to the bottoms of closed-well micro-well plates or multi-well tissue culture plates, for example. Each microfluidic chip may be in a unique well or assay region or across a plurality of wells or assay regions. Each unique vascular network with or without tissue spaces can be considered to be a unique microfluidic chip. As such, multiple microfluidic chips can be fluidly linked together with fluid pathways that extend between the unique wells and assay regions. In many cases, however, it is preferable to distribute the microfluidic chips on a solid, flat, and optically transparent substrate of a microfluidic device 131. As shown, FIGS. 10A and 10B illustrate exploded views of two embodiments of microfluidic devices 131 having an array of microfluidic chips or networks. Each individual microfluidic network can be referred to as a microfluidic chip 135, configured to operate with the microfluidic device 131, such as, for example, a 24-open bottomless well plate format.

FIG. 10A shows the microfluidic device 131 that is prepared from a substrate 132, a well plate 133, and a manifold 134 coupled together. These components can be affixed, combined, integrated, or otherwise joined together as separate parts or formed from a unitary member. For example, the substrate 132 and the well plate 133 can be a single body member that is coupled with the manifold 134. In another example, the well plate 133 and the manifold 134 can be a single body member that is coupled to the substrate 132. In another example, the substrate 132, the well plate 133, and the manifold 134 can be a unitary body member, which can be prepared by advanced 3-D printing techniques. However, the substrate 132, the well plate 133, and the manifold 134 can be prepared as three separate members and joined together.

The substrate 132 is shown to include the microfluidic chips 135. Each microfluidic chip 135 can be a vascular network with or without extravascular spaces (e.g., tissue spaces). The microfluidic chips 135 can be isolated or combined with other microfluidic chips 135. The microfluidic chips 135 can correspond with one or more wells 138 of the well plate 133 as described below, which can include vascular network or extravascular space extending between one or more wells 138. While FIG. 10A shows each microfluidic chip 135 corresponding to one well 138, FIG. 10B shows a single microfluidic chip 135a corresponding to a plurality of wells 138. The microfluidic chips 135 can be formed into or integrated in the substrate 132, or the microfluidic chips 135 can be separate members that are bonded or reversibly attached by means of a vacuum or mechanical clamps or magnetic clamps to a flat, optically transparent substrate 132.

The well plate 133 can be configured as any standard well plate with one or a plurality of wells 138 in a body. The wells 138 can have an opening in the top and bottom of the well plate 133. The bottom opening of each well 138 allows for the well to correspond with at least a portion of the microfluidic chip 135. The top opening allows for well channels 136 to extend through the wells 138. The well channels 136 can be coupled to the manifold 134 as illustrated and described. The well plate 133 can have a number of wells 138 to correspond with standard well plate readers. The well plate 133 is dimensioned with the substrate 132 so that they can be integral or coupled together.

The well channels 136 can be any type of tube that extends through the well 138 so that fluid can be administered to the microfluidic chips 135 and withdrawn therefrom. As such, the well channels 136 can include an inlet channel 136a and an outlet channel 136b. While the length of the inlet channel 136a and the outlet channel 136b can extend into the vascular network of the microfluidic chip 135, any length can be used. The inlet channel 136a and the outlet channel 136b can be used to deliver or withdraw any fluid, such as biological test fluids or air.

The manifold 134 can be configured as a body having one or more individual manifold channels 137. The manifold channels 137 can be fluidly coupled with the well channels 136. As such, the inlet channel 136a can be coupled with an inlet manifold channel 137a and the outlet channel 136b can be coupled with an outlet manifold channel 137b. Each inlet manifold channel 137a can be fluidly coupled to one or more inlet channels 136a. Each outlet manifold channel 137b can be fluidly coupled to one or more outlet channels 136b. While the manifold 134 is shown to be a body having fluid conduits as the manifold channels 137, the manifold may be a collection of tubes with or without a body containing the same, where the tubes can be configured and arranged to provide the fluid delivery and withdrawal.

The embodiments can include the microfluidic chips 135 formed or coupled to the substrate 132, with a manifold body having inlets and outlets for each microfluidic network coupled with the substrate. Also, each unique well or assay region can be associated with a manifold body having inlets and outlets. Also, a plurality of fluidly linked wells or assay regions can be associated with the manifold body having inlets and outlets. The unique wells or assay regions can each receive a fluid inlet and a fluid outlet. Alternatively, a plurality of linked wells or assay regions can receive a single fluid inlet or a single fluid outlet.

Figure 11:
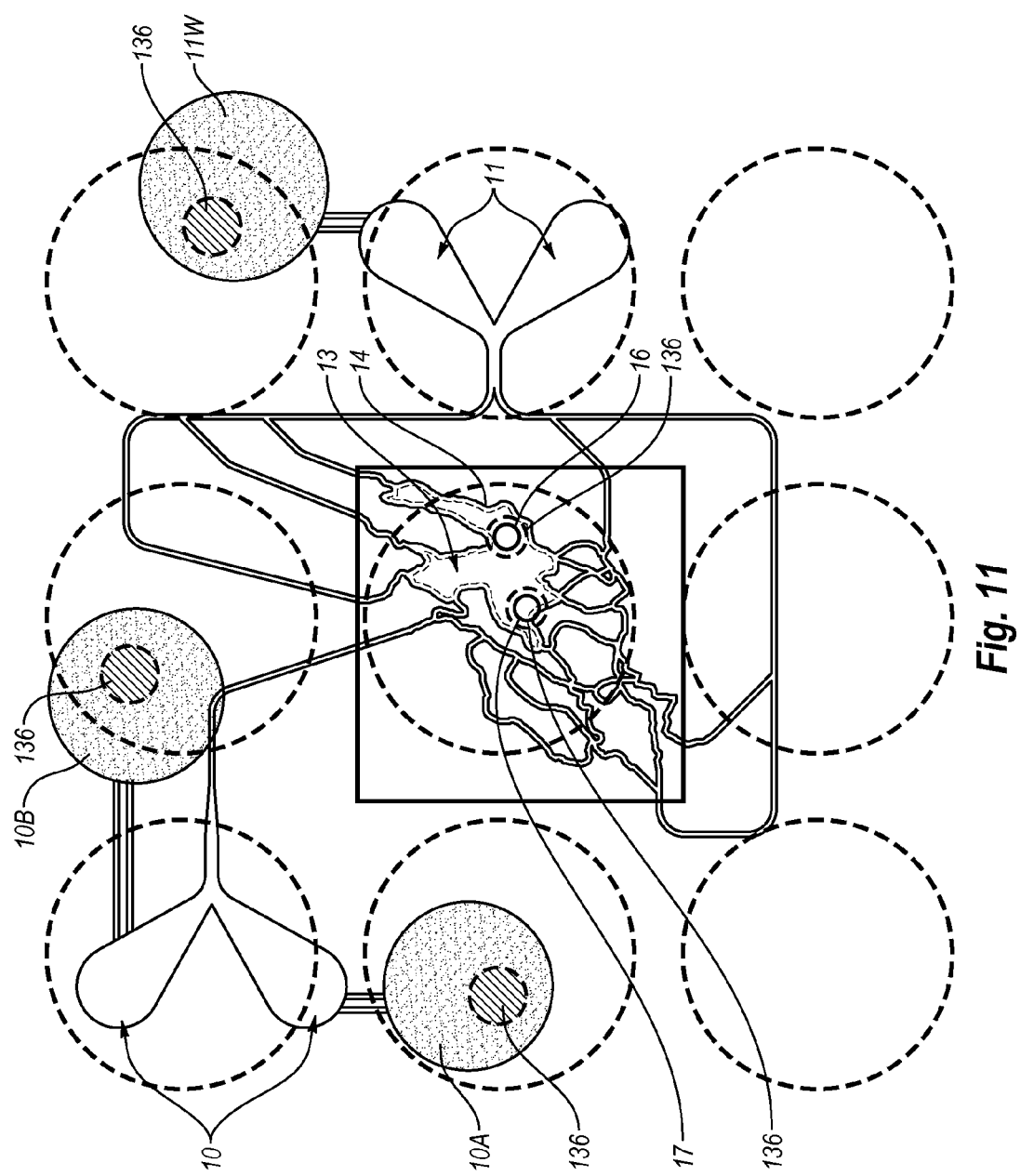
FIG. 11 illustrates an embodiment of a portion of a device having a microfluidic network comprising a SMN and having a footprint corresponding to nine wells of a multi-well plate.

The microfluidic chips 135 may correspond 1 to 1 with wells of a 24-well array as shown in FIG. 10A or other well plate array, or one or more microfluidic chips 135 may be sized so as to overlap a plurality of wells in the 24-well array as shown in FIG. 10B. The arrays of microfluidic chips may be configured to fit within or overlap wells from various micro-well plates including 96-well plates. FIG. 11 shows a top view of a microfluidic chip arrangement in which the footprint of a microfluidic chip overlaps multiple wells.

Microfluidic chip arrays may include SMN- and/or IMN-containing microfluidic chips. The microfluidic chips in an array may all have the same footprint or different footprints. For example an array may comprise microfluidic chips having a footprint corresponding to two wells of a 24- or 96-well bottomless plate, each containing an IMN connected to two inlet linking channels through a first well and an outlet linking channel through a second well.

Inlet and outlet ports of the SMN-, IMN-, and/or bifurcation-containing microfluidic chips are fluidically coupled with a fluidic manifold 134 containing manifold channels 137 through at least two well channels 136, one for inflow and one for outflow. Additional manifold and linking channels may be included, for example, to deliver fluid to and receive fluid from extravascular tissue spaces. The well channels 136 are shown as being contained in the well plate 133 that is separate from the fluidic manifold 134. Coupling means such as compression fitting, barb fittings, or mechanical clamps or magnetic clamps, or any other means may be used to form fluid-tight linkages between inlet/outlet ports, inlet/outlet linking channels, and/or inlet/outlet manifold channels. The well plate 133 and the fluidic manifold 134 may be embodied as a single manifold in which linking and manifold channels are unified.

SMN chips integrated or coupled with microwell plates may comprise separate pairs of ports for inflow and outflow for cell seeding and introducing and removing other assay reagents. This ensures that the ports for pumping reagents for assays do not contain cells. Valves may be used to regulate flow to desired inlet/outlets. The inlet/outlet ports from each of the SMN devices may be interfaced with a corresponding custom manifold for fluidic connections to ensure that each of the wells can be operated individually or simultaneously depending upon the wells needed for the assay. Placing a valve between the inlet manifold and each inlet to each microfluidic chip, for example, allows each of the microfluidic chips to be operated individually or simultaneously. For an embodiment comprising a microfluidic chip spanning across two or more wells of a multi-well plate, valves located to the inlet at each well may be used to control flow to different inlets on the same microfluidic chip. Separate reservoirs for priming buffer, matrix-forming reagents, cells, cell media, test sample, and wash buffer are preferably provided, but are not shown in the figures for the sake of clarity. Preferably well plates have designated reservoir wells to eliminate the need for a secondary set of off-chip reservoirs.

FIG. 11 shows a top view of one of a number of microfluidic chips in an array. The microfluidic chip contains a SMN and has a footprint corresponding to nine wells of a 96-well bottomless microtiter plate. The microfluidic chip is fixed on a flat substrate, as shown in FIG. 10B, and comprises a network inlet 10, a network outlet 11, and an extravascular tissue space 13. The network inlet is connected to first and second reservoirs 10a, 10b which, in turn are in fluid communication with two inlet well channels 136 located in separate wells of a linking manifold. The network outlet 11 is connected to a waste reservoir 11w, which is in fluid communication with a well channel 136. The ports 16 and 17 of extravascular tissue space 13 are connected with well channels 136 through another well. The well channels 136 are contained in a linking manifold as shown in FIGS. 10A and 10B. Each linking channel is fluidically coupled to fluidic channels in a fluidic manifold (FIGS. 10A and 10B). The fluidic channels in the fluidic manifold delivering fluid to the microfluidic chip are fluidically coupled to pumping means configured to pump fluid from the network inlet of the microfluidic chip to the outlet. Eight microfluidic chips as shown in FIG. 11 may be accommodated in an 8×12 96-well format.

Assay Apparatus

Figure 12:
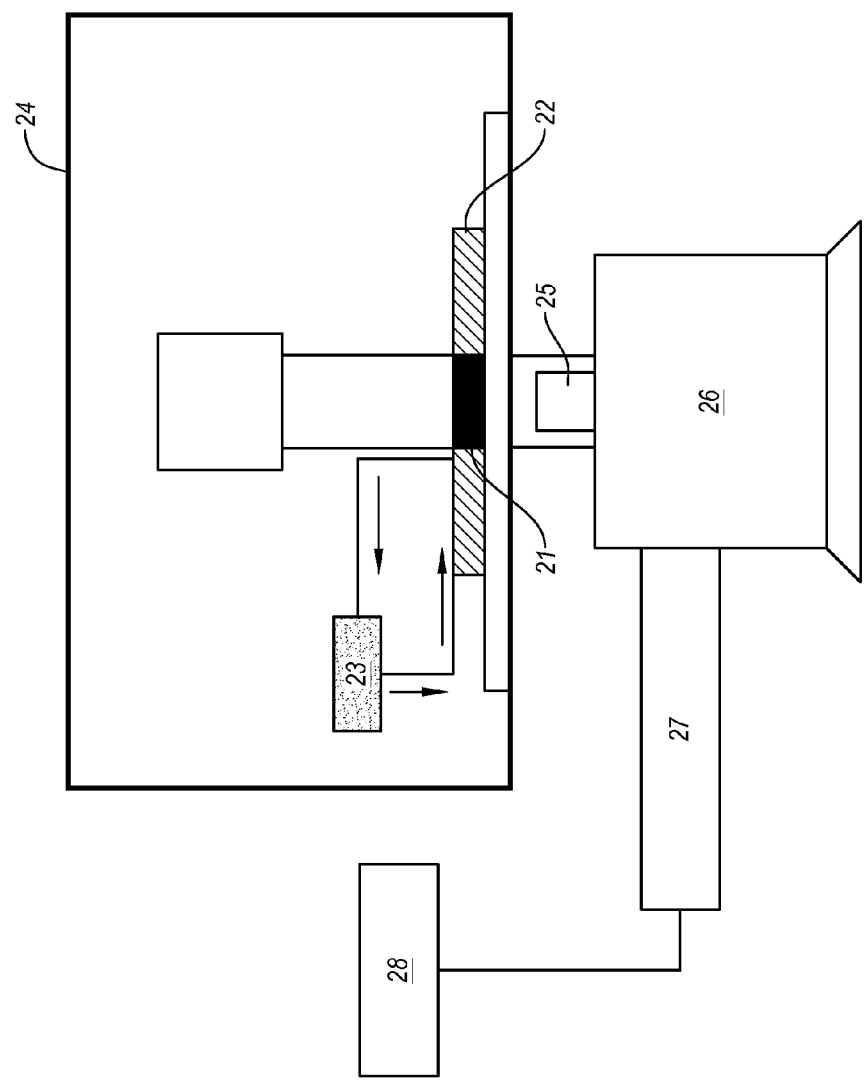
FIG. 12 illustrates an embodiment of an assay apparatus for use with microfluidic chip arrays.

An example of an assay apparatus to be used in combination with microfluidic chip arrays is shown in FIG. 12. The apparatus comprises one or more pumping means 23 such as a peristaltic pump, a pneumatic pump, or a syringe pump to move fluids through one or more microfluidic chip arrays 21 placed on an automated stage device 22. The microfluidic chip arrays 21 may be contained within an incubation chamber 24 and are positioned over an objective lens 25 of a brightfield, phase contrast, or fluorescent microscope 26. Optical means such as a CCD camera or video camera 27 are used to visualize cells within each microfluidic chip in the microfluidic chip arrays 21. The camera 27 is in communication with a computer 28 for data collection and control of the microscope 26, the stage device 22, the camera 27, and microscope mounted accessories.

Means for collecting data from the microfluidic chip array may comprise an optical module for visualization and/or a plate reader configured to detect a fluorescence, luminescence, or other electromagnetic signal. A light source or laser may be provided as part of an optical or fluorescence detection and data collection means. An automated stage provides precise and repeatable control of microfluidic chip locations. All systems including pumps, stage, detection means, data collection and processing, valves, fluidic arm, and incubator are preferably, but not necessarily, controlled in an integrated fashion by a single computer.

Assays

A wide variety of assays may be performed using microfluidic chips comprising SMNs with or without tissue spaces. Several examples of such assay are disclosed in U.S. Pat. Nos. 8,380,443; 8,175,814; and 7,725,267, all of which are incorporated by reference herein in their entirety.

Example: Particle Adhesion Assays

Fluorescently-labeled polystyrene beads are coated with anti-P-selectin antibodies and passed through SMN chips using different shear rates. The fluorescence measured within each SMN is used to determine the percentage of particles adhering to the walls of the network at five different shear rates.

Fluorescently-labeled polymer particles having elliptical shapes with a range of aspect ratios of from 1:1 to 6.5:1 are passed through chips comprising SMNs and chips comprising linear, non-bifurcating channels. The fluorescence measured within each SMN is used to determine the percentage of particles adhering to the walls of the network for four different aspect ratios.

Red fluorescently-labeled polystyrene beads coated with anti-ICAM-1 antibody and green fluorescently-labeled polystyrene beads coated with nonspecific IgG are injected into different microfluidic chips comprising SMNs coated with endothelial cells activated with TNF-α for four hours, 24 hours, or not at all. Fluorescence microscopy is used to quantify the number of particles bound to the walls of selected regions within each of the SMNs.

The delivery of DNA containing a therapeutic gene and green fluorescence protein (GFP) gene to HeLa cells cultured on the luminal surfaces of SMNs by a lipopolymer is assayed by detecting the fluorescence produced by GFP expressed inside the HeLa cells.

Example: Leukocyte Adhesion Cascade (LAC) Assay

Figure 13:
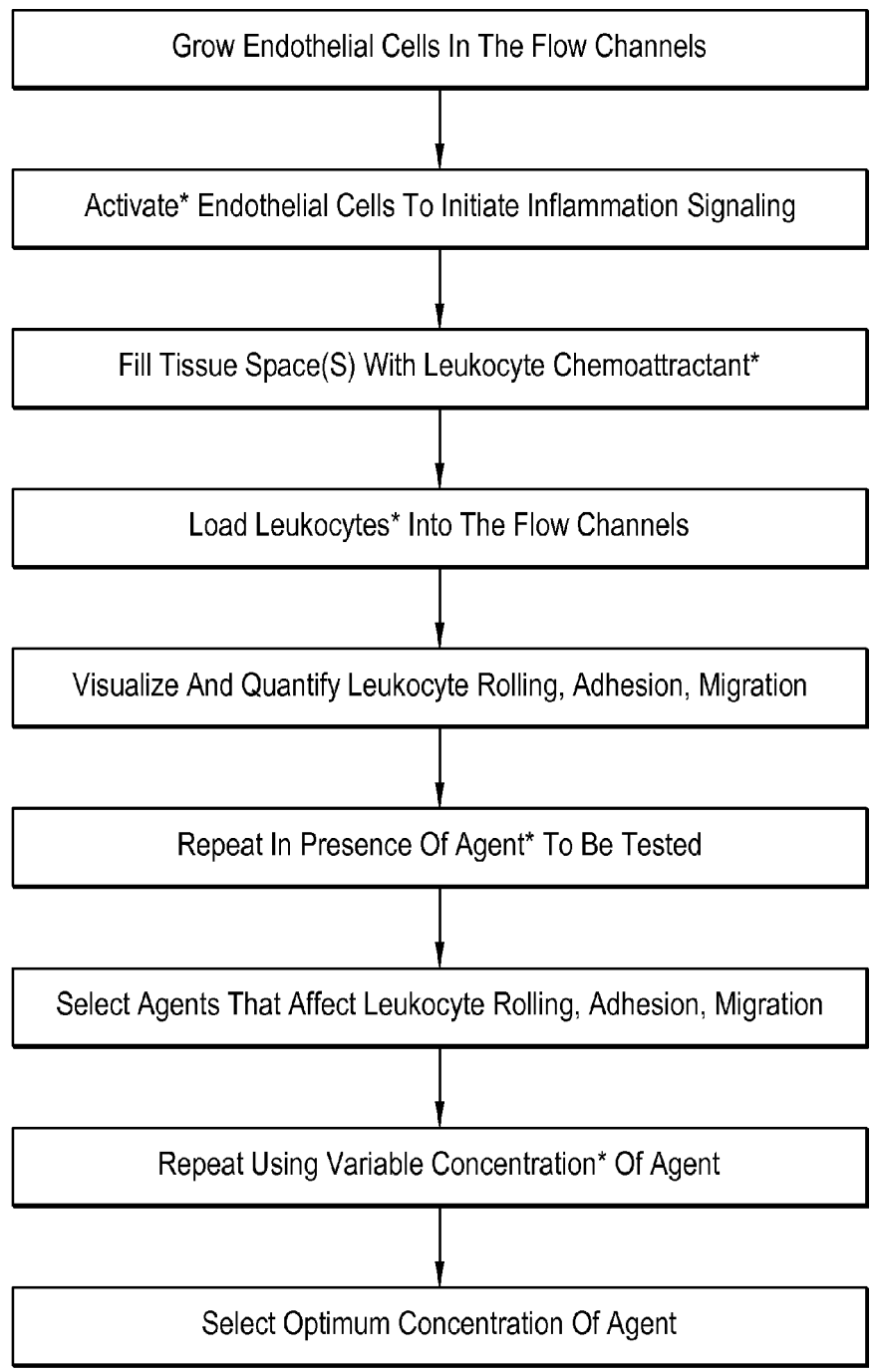
FIG. 13 includes a flow diagram showing assay steps for leukocyte adhesion.

Method steps comprising a LAC assay adapted for a SMN microfluidic chip array are provided in FIG. 13. In this example, the array comprises microfluidic chips comprising a SMN. Asterisks in FIG. 13 indicate parameters that may be varied across microfluidic chips in an array. The flow channels are first coated with an extracellular matrix protein and/or proteoglycan to facilitate cell adhesion, and are then coated with a confluent layer of primary endothelial cells or a cultured endothelial cell line. The endothelial cells are activated before leukocytes are introduced into SMNs on microfluidic chips in an array. Variability between microfluidic chips in an array and/or SMNs within a microfluidic chip may include the method, agent, and/or duration of endothelial cell activation.

Pores and, optionally, extravascular tissue spaces may be filled with a gel to provide a medium through which leukocytes can migrate. For stimulating leukocyte migration, a source for a leukocyte-attracting cytokine or other leukocyte chemoattractant may be introduced into at least one extravascular space. Variability between microfluidic chips may include the identity and/or concentration chemoattractant used. A suspension of leukocytes is introduced into the device and allowed to circulate or allowed to incubate, depending on the purpose of the assay. Leukocytes may be recirculated through the device at a single or multiple flow rates to assess the effect of shear forces on leukocyte rolling, adhesion, and/or migration modulation. Variability between microfluidic chips in an array and/or SMNs within microfluidic chips may include various pretreatments of leukocytes before loading, flow rates, and/or shear forces during recirculation and duration of recirculation. The locations of leukocytes and numbers of leukocytes in different locations within the device over time are captured by digital camera or other optical means and stored in a computer. The degree of leukocyte rolling, adhesion, and/or migration modulation is measured by comparing the numbers of leukocytes located at various positions in the device over time and providing end point and kinetic values for leukocyte cascade activation. Leukocytes may be introduced into the chip at desired time points following activation to reproduce the complete adhesion cascade. One or more chemoattractants may be introduced into one or more extravascular tissue spaces to stimulate migration. Rolling, adhesion, and migration of leukocytes into the one or more extravascular tissue spaces may be captured in real time by scanning the entire network. Drug screening may be performed, for example, by the injection of potential cascade inhibitors to analyze the effect on adhesion and migration.

Example: Tumor Drug Delivery Assay

Figure 14:
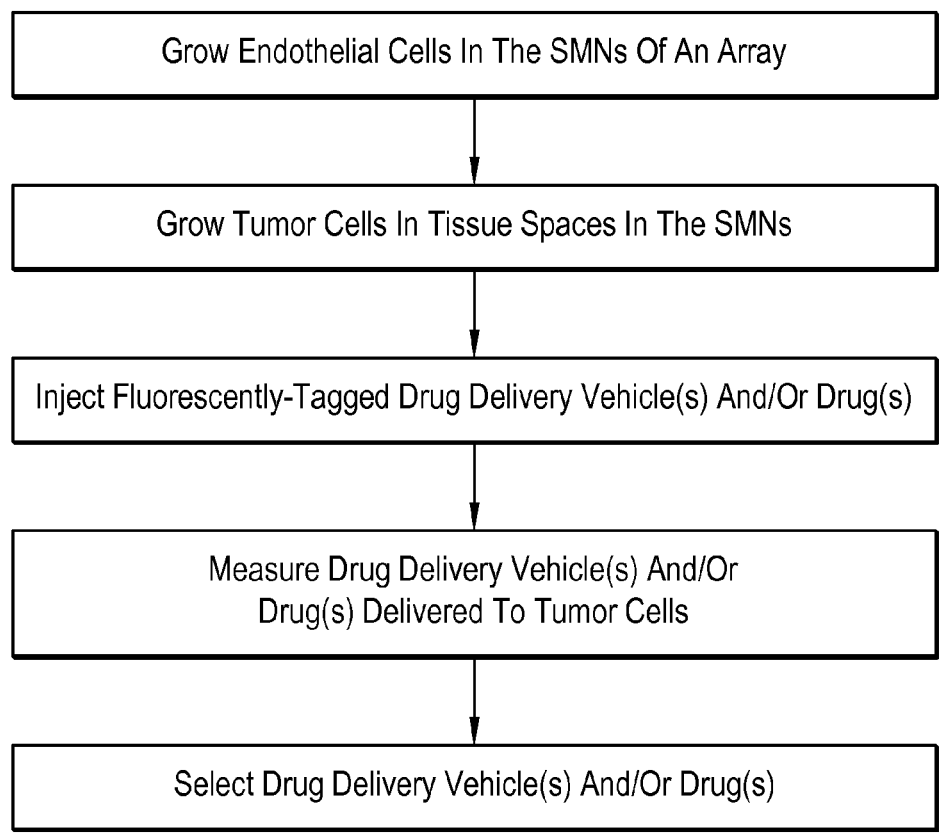
FIG. 14 includes a flow diagram showing assay steps for tumor drug delivery.
Figure 15:
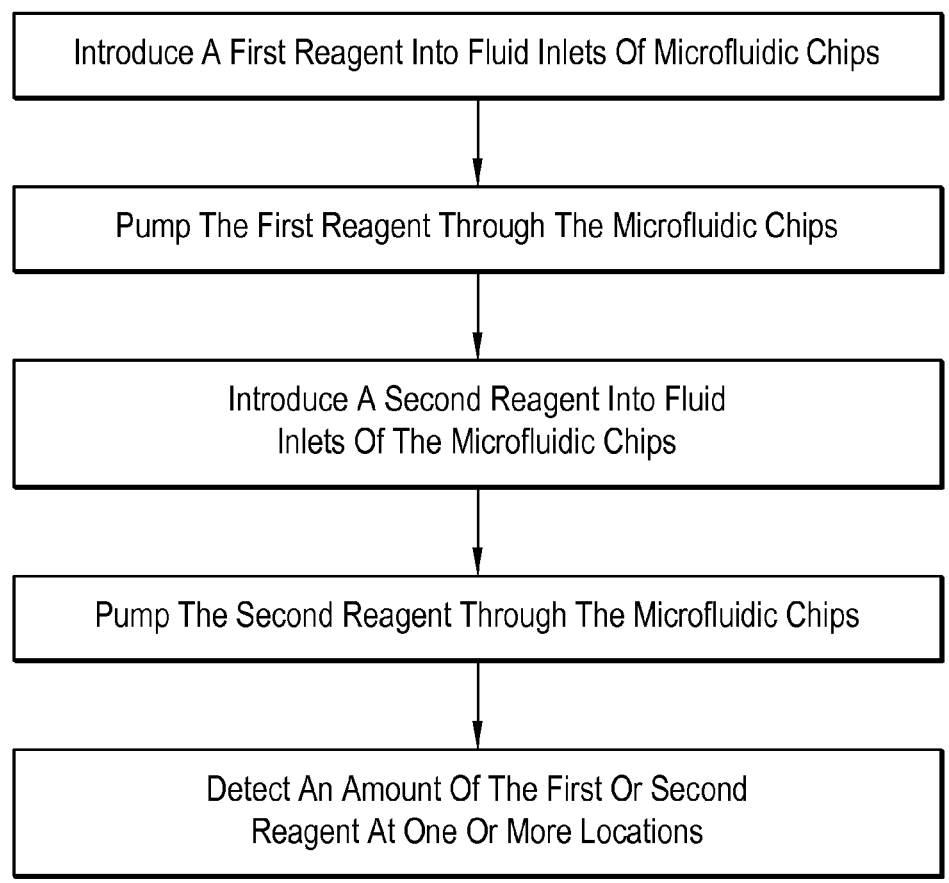
FIG. 15 includes a general flow diagram showing assay steps of the invention.

FIG. 14 shows method steps for each microfluidic chip in a microfluidic chip array in a screening method for identifying one or more drug delivery vehicles for tumor drug delivery. Examples of drug delivery vehicles include eukaryotic cells, prokaryotic cells, natural and recombinant viral vectors, liposomes, lipopolymers, polymer beads, nucleic acids including DNA and RNA, and functionalized and nonfunctionalized synthetic polymer molecules. The microfluidic chips in this example all contain one IMN comprising one extravascular tissue space. Another example may use microfluidic chips comprising one or more SMNs and or IMNs, each comprising one or more extravascular tissue spaces. Different fluorescently tagged drug delivery vehicles are introduced into different network inlets at one shear rate or variable shear rates. A range of shear rates from 0-500 $sec^{-1}$ may, for example, be established among the chips in the network and the flow maintained in circulation for four hours. Every 30 minutes each network is scanned to assess the fluorescent intensity in the tissue space of the network. A higher intensity of the drug delivery vehicle in the tissue space with the tumor cells indicates a more effective transport of the vehicles to the tumor location. Degradation of the delivery vehicles is monitored in the flow channels of the chips by analyzing loss of intensity of circulating vehicles, and aggregation is monitored by visualization of clumping of delivery vehicles. Identities and concentrations of the delivery vehicles and shear rates are correlated with tumor drug delivery to determine the effects of delivery vehicle concentration and shear rates on stability, aggregation, and delivery. The experiment may also be conducted or repeated with the drug delivery vehicles suspended in whole blood, apheresed blood, and in media containing white blood cells, red blood cells, and/or platelets.

Example: Adhesion Assay on Bifurcating Channels Coated with Proteins

In this example, the array of microfluidic chips comprises microfluidic chips, each containing an IMN network as shown in one of FIGS. 7A-7C coated with a protein. A suspension of polystyrene beads of desired size is coated with antibodies that bind to the protein coating the IMN network channels. A PBS solution is applied via a fluidic manifold to each of the IMN inlet openings. Desired experimental areas corresponding to the IMNs in the array are then programmed into a stage movement controller and stored. Variable concentrations of antibody-coated particles of from $5 \times 10^3$/ml to $5 \times 10^7$/ml are pumped into the IMN inlets at a flow rate corresponding to a shear rate of 500 $sec^{-1}$. Shears are then varied from 500 $sec^{-1}$ to 7.5 $sec^{-1}$ in between group of chips. Every three minutes, an image is taken of each chip. The images are post-processed with specific Areas of Interest (AOIs) ranging from μm to mm size, depending on chip and channel dimensions, to yield the counts of particles adhered at each of the selected locations. A plot of shear vs. particles bound per unit area is plotted for each of the locations and particle concentrations to yield a shear-adhesion map.

Example: Adhesion Assay on Channels Coated with Cultured Cells

An array of eight microfluidic chips is prepared by affixing the microfluidic chips on a transparent glass or plastic plate as shown in FIG. 10B and placed on an apparatus as shown in FIG. 12. Each microfluidic chip comprises one SMN and is sized to have a footprint corresponding to nine wells of a 96-well bottomless microtiter plate in a square pattern. Cell culture matrix comprising gelatin and fibronectin in cell culture medium is injected into the network inlets of the SMNs at a flow rate of 10 μl/min for 10 min and incubated for two-four hours. Cells at a concentration of $1 \times 10^5$/ml-$5 \times 10^7$/ml are pumped into the network inlets of the SMNs. The cells are continuously perfused with media at shear rates of 7.5-500 $sec^{-1}$ until they are 80% confluent. The cells are then activated by including a cytokine (e.g., TNF-alpha, IL-1beta) in the cell media for six hours. The locations of the SMN areas are programmed into a stage movement controller of an automated microscope stage and stored.

Fluorescently labeled polystyrene beads of different sizes coated with antibodies to an upregulated adhesion molecule such as E-Selectin or ICAM-1 are pumped into the network inlets of different microfluidic chips. Every three minutes, an image is taken of the entire chip or of key locations using an automated stitching procedure. The images are post-processed with specific AOIs ranging from μm to mm size to yield the counts of particles adhered at each of the selected locations. A plot of polystyrene bead size vs. particles bound per unit area is plotted for each of the locations to produce a size-adhesion map. In addition, one can create shear-adhesion maps for the particles bound per unit area vs. shear ranges.

Example: Particle Uptake Study on Channels Coated with Cultured Cells

A cell culture matrix comprising gelatin and fibronectin in cell culture medium is pumped into the inlets of an array of 24 microfluidic chips as shown in FIG. 6 arranged in a 24-well bottomless format as shown in FIG. 10A on an assay apparatus as shown in FIG. 12. The array is incubated in a cell culture incubator for two-four hours. Cells at a concentration of $1 \times 10^5$/ml are pumped into the microfluidic chips of the array and are continuously perfused with media at a shear rate of 7.5-500 $sec^{-1}$ until the cells are 80% confluent. Desired experimental areas including the middle of each parent channel, the junction, and the middle of each of the daughter channels are programmed into the stage movement and stored.

Drug delivery vehicles encapsulating a fluorescent tag are pumped into the inlets of the different microfluidic chips at shear rates ranging from 500 $sec^{-1}$ to 7.5 $sec^{-1}$. Every four hours, an image is taken of the entire chip or of the key locations using an automated stitching procedure. The images are post-processed with specific ROIs ranging from μm to mm size to yield % of cells that have taken up particles. A plot of shear vs. % of cells (at each location) expressing moieties taken up is then calculated.

Particular embodiments of the invention are described and illustrated in the drawings. Specific terminology is employed for the sake of clarity, but the invention is not intended to be limited to the specific terminology used and it is to be understood that each specific element includes all technical equivalents that operate in a similar manner to accomplish a similar purpose. The terms used herein are intended to have their conventional meanings as understood by a person of ordinary skill in the art, as supplemented by the definitions provided.

A synthetic microvascular network array comprising two or more optically transparent plastic microfluidic chips, said microfluidic chips each comprising at least one chip fluid inlet, at least one chip fluid outlet, and a plurality of idealized or non-linear flow channels forming a synthetic microvascular network wherein the synthetic microvascular network comprises a network fluid inlet and a network fluid outlet and each of said idealized or non-linear flow channels forming said synthetic microvascular network has a maximum cross-sectional dimension of between 2 µm and 500 µm and possesses a geometric characteristic selected from the group consisting of a variable cross-sectional shape, a variable cross-sectional area, a turn, a bend, a bifurcation, a junction, a convolution, an inflection point, an anastomosis, and combinations thereof. Optionally, at least one of the non-linear flow channels forming said synthetic microvascular network comprises an anastomosis or a convolution. Optionally including a microwell plate and wherein the two or more microfluidic chips are irreversibly bonded with or reversibly attached to the microwell plate. Optionally including a means for detecting an optical or fluorescent signal from or means for detecting impedance within the two or more microfluidic chips. Optionally, the chip fluid inlets of said two or more microfluidic chips are connected to an array inlet manifold that is configured to deliver liquid to the chip fluidic inlets of said microfluidic chips and the chip fluid outlets of the microfluidic chips are connected to an array outlet manifold that is configured to receive liquid from the chip fluidic outlets of said microfluidic chips. Optionally, the device or system thereof can include two or more reservoirs and a pumping means configured to pump liquid through the two or more microfluidic chips and wherein said pumping means is configured to pump fluid from the two or more reservoirs into the array inlet fluidic manifold. Optionally, the two or more reservoirs contain different fluids and the array further comprises valves configured to selectively pump fluid from one of the two or more reservoirs through one or more of the microfluidic chips. A system can include a computer wherein said valves, said pumping means, and said means for detecting an optical signal or means for detecting a fluorescent signal are controlled by said computer. Optionally, luminal surfaces of the flow channels are coated with a substance selected from the group consisting of a chemical, a biomolecule, a cell, and combinations thereof. Optionally includes a stage upon which the array is placed and wherein the stage is configured to control the movement and location of the array. Optionally, at least one of said synthetic microvascular networks further comprises a tissue space, a tissue space inlet, and a tissue space outlet wherein said tissue space is in fluid communication with a fluidic manifold through the tissue space inlet and the tissue space outlet, has cross-sectional luminal dimensions of between 100 µm and 1 cm, and is separated from a lumen of at least one flow channel by a porous wall comprising pores having maximum cross-sectional dimensions of between 0.2 µm and 30 µm and is in liquid communication with said flow channel through said porous wall. Optionally, the luminal surfaces of the flow channels are coated with cells. Optionally, further comprises cells in the lumen of the tissue space. Optionally, the tissue space contains one or more substances selected from the group consisting of an extracellular matrix, a basement membrane, a cytokine, a cell that secretes a cytokine, a gel, a cell culture, a source of a leukocyte chemoattractant, and combinations thereof. Optionally, the pores are filled with a substance selected from the group consisting of a gel, a basement membrane, an extracellular matrix, a tissue matrix, a synthetic matrix, a natural matrix, and combinations thereof.

In one embodiment, a method for performing an assay can include the steps of: a) introducing liquid containing a first reagent into fluid inlets of at least two microfluidic chips of a synthetic microvascular network array as recited herein; b) pumping the liquid containing the reagent through the microfluidic chips from the fluid inlets to fluid outlets; and c) detecting an amount of the first reagent or effects caused by the reagent at one or more locations within the microfluidic chips. Optionally, wherein at least one of the synthetic microvascular networks comprises a tissue space, a tissue space inlet, and a tissue space outlet wherein the tissue space is in fluid communication with a fluidic manifold through the tissue space inlet and the tissue space outlet, has cross-sectional luminal dimensions of between 100 µm and 1 cm, and is separated from a lumen of at least one flow channel by a porous wall comprising pores having maximum cross-sectional dimensions of between 0.2 µm and 30 µm and is in liquid communication with said flow channel through said porous wall. Optionally, the first reagent is selected from the group consisting of a cell, a drug, a drug carrier, a particle, and combinations thereof and wherein an amount of the reagent is detected in a tissue space or in one or more flow channels within the synthetic microvascular network. Optionally, further comprises introducing a second liquid containing a second reagent into fluid inlets of at least two microfluidic chips of a synthetic microvascular network array and pumping the second fluid through the microfluidic chips. Optionally, the second reagent is introduced into the same fluid inlets as the first reagent. Optionally, the second reagent is introduced into the different fluid inlets from the first reagent and into the same microfluidic chips as the first reagent. Optionally, the second reagent is introduced into the different fluid inlets from the first reagent and into different microfluidic chips from the first reagent. Optionally, the amount of the reagent detected at one or more locations within the micro fluidic chips is detected by measuring an optical or fluorescent signal from or an impedance within the microfluidic chips. Optionally, at least one of the microfluidic chips comprises a tissue space, a tissue space inlet, and a tissue space outlet wherein the tissue space is in fluid communication with a fluidic manifold through the tissue space inlet and the tissue space outlet, has cross-sectional luminal dimensions of between 100 µm and 1 cm, and is separated from a lumen of at least one flow channel by a porous wall comprising pores having maximum cross-sectional dimensions of between 0.2 µm and 30 µm and is in liquid communication with said flow channel through said porous wall. Optionally, the liquid containing the reagent is pumped through the microfluidic chips using a flow scheme selected from the group consisting of single pass, multiple passes, a recirculating circulation loop, and combinations thereof. Optionally, further comprises the step of measuring a property of the reagent, said property selected from the group consisting of real-time circulation, stability, half-life, aggregation, degradation, and combinations thereof. Optionally, the liquid containing the reagent is pumped through the microfluidic chip using varying fluidic shear rate values of between 1 sec$^{-1}$ and 5000 sec$^{-1}$. Optionally, the liquid containing the reagent comprises a component selected from the group consisting of cell culture media, a buffer, serum proteins, whole blood, apheresed blood, eukaryotic cells, bacteria, leukocytes, erythrocytes, platelets, viruses, and combinations thereof. Optionally, the liquid containing the reagent is pumped through the microfluidic chips by electrokinetic and/or electrothermal pumps located in the microfluidic chips, and/or a pumping mechanism fluidically connected to the inlets and/or outlets of the microfluidic chips.

The devices and methods involving a microfluidic chip array containing microvascular networks can be used together with a microfluidic control system configured for performing a variety of high-throughput assays. The arrays can be configured for use with microwell plates, an automated assay system, and visual or other detection means for collecting data. The devices and methods are useful for a variety of assays, including those that associate local hemodynamic factors such as wall shear stress, dynamic pressure, and residence time with particle adhesion on, uptake into, and transmigration through cells lining walls in the synthetic microvasculature.

In one embodiment, as assay region described herein can be considered to be a well, or arranged or located in a well location with respect to a multi-well plate or plate reader. Each microfluidic network includes at least one assay region. Multiple assay regions can be connected by fluidic flow paths in the substrate to "daisy-chain" the assay regions together. As such, the multiple wells can be connected by the flow paths in the substrate between the wells. The inlet and outlet manifolds with the plurality of inlet conduits or outlet conduits may also fluidically couple wells, as shown in FIGS. 10A and 10B. The entire rows or columns can be fluidly coupled as shown. This allows for parallel assays to be run on a single plate, where the assays can be the same or have difference between them. The differences can be in the configuration of the microfluidic networks, types of tissue chambers, types of cells, or types of test analyte. Control analytes may also be used in one or more microfluidic networks, such as in the networks shown to be connected with the manifold system.

The incorporated references describe idealized microvascular networks (IMN) and synthetic microvascular networks (SMN), which can be included in the inlets, outlets, or chambers therebetween. The microfluidic networks of the cell culture device can be configured with IMN and/or SMN flow paths and chambers. Some configurations can include only IMN, some may include only SMN, and some can include a combination of both IMN and SMN. For example, the cell culture device can simulate the liver, kidney, heart, lung, brain, blood brain barrier, vascular networks, or others. As such, the distinct microfluidic networks can have unique cell cultures that are indicative of the different cell types or tissue types of an organ. A single embodiment of the cell culture device can be configured to include simulations of different organs by the different cells or cell combinations in the distinct cell cultures of the distinct chambers. That is, different types of cells and cell combinations can distinguish a microfluidic network or tissue chamber thereof simulating the heart from a device simulating the liver, where without the cells the devices can appear similar or identical.

The cell culture device can be configured to be retained in any common cell culture incubator or other common laboratory equipment used for growing, propagating, and analyzing cell cultures. The inlets and outlets can be configured to be coupled to tubing, cell culture pumps, syringe pumps, or other cell culture equipment or pumps that can move fluid through the fluid inlets and outlets as well as through the distinct chambers. Unique pumps can be coupled to the different chambers. While not specifically shown, the inlets and outlets may each individually include inlet valves and outlet valves, which can be selectively opened to allow fluid flow or pressure and closed for incubation.

In one embodiment, the distinct tissue chambers or microfluidic pathways of a microfluidic network can have different cells or cell combinations for different cell cultures. The cell culture of each microfluidic pathway or tissue chamber can have a distinct function.

The tissue chambers are separated from the microfluidic pathways by porous walls. The walls between any microfluidic pathway and tissue chamber (e.g., organ tissue chamber) can be porous so that fluid and/or nutrients can pass therebetween. In one option, the pores can be a dimension that is too small for cells to pass through; however, the pores can be enlarged in some embodiments so that cells may pass therethrough such as when modeling cancer cell movement or metastasis or leukocyte migration and other conditions. In any event, various analytes, such as test analytes and metabolic analytes, can pass through the pores of the porous walls. The dimension of the pores can vary. For example, the dimension of the pores can have a dimension up to 50 microns and as small as 100 nm; however, the dimension can range from about 200 nm to about 30 microns. The larger pores can be for cancer tissue simulations and allow for metastasis or cancer cells migrating between tissue chambers. Generally, the pores can be smaller than 20 microns or smaller than 2 microns to inhibit cell migration therethrough.

The dimensions of the microfluidic pathways can range from about 5 microns to about 500 microns, and possibly up to 1000 microns. The separation dimension between walls of a pathway can be about 10 microns, about 100 microns, about 200 microns, about 250 microns, or about 400 microns, or any dimension therebetween. In one example, the height of the microfluidic pathways can be about 5 microns to about 150 microns. The perforated walls separating a microfluidic pathway and tissue chamber can have a thickness that generally ranges from about 5 microns to about 500 microns, or such as, for example, 1 micron, 10 microns, 20 microns, 30 microns, or up to 100 microns. Each microfluidic pathway or tissue chamber can be large enough to culture enough cells to get some meaningful data during an assay, but the tissue chambers should not be too large where diffusion times are too great and inhibit obtaining meaningful data.

The porous walls can be configured to provide a diffusion barrier between the microfluidic pathways and tissue chambers. This can provide a diffusion barrier between the vascular space (e.g., microfluidic pathway) and tissue space (e.g., internal organ tissue chamber).

The internal chamber can be wider with a larger cross-sectional profile than the microfluidic pathways. The cross-sectional profile or distance between the porous internal walls of a tissue chamber can be from about 1.5 to 50 times larger than the microfluidic pathways cross-sectional profiles or width thereof.

The cells can grow only on the bottom, or can grow to confluence on the sides and optionally the top walls of the microfluidic pathways and tissue chambers. As such, the cells can grow over the pores. Preferably, the cells grow completely around the tissue chambers and/or microfluidic pathways to form a cellular lumen or three-dimensional tissues. Tissue culture scaffold materials can be located in any or all of the tissue chambers and/or microfluidic pathways as desired. The cells can grow over the pores but allow analytes or metabolites or other fluid to pass through the pores to an adjacent chamber. So, the cells start growing at the bottom first, but eventually they fill up the porous side walls and the top walls and all around the chambers and microfluidic pathways.

Each tissue chamber can provide a tissue space that includes tissue culture scaffolds that will help grow the cells in a pseudo 3-D sense to substantially fill up the entire space of the chamber. Otherwise the cells will just cover the walls (e.g., bottom, side, and/or top). Whereas the tissue scaffolds provide a 3-D cell culture in a nice, packed structure in the tissue space. The scaffolds can be the same or different material from the walls. The scaffolds can be integrated or coupled with the walls, or inserted into the chambers. The scaffolds can be cast in the same method when the walls of the chambers are cast.

The substrate of the cell culture device can be manufactured in accordance with known principles, such as in the incorporated references. The devices can be made by providing a stamp and then pouring a polymer over it, then bake or otherwise cure the polymer so the polymer hardens, and then peeling the polymer from the stamp (e.g., mold). There can be a negative of the device on the stamp, which provides the device when cast with the polymer. The device can then be attached to a top wall, such as polymer or glass, or an intermediate body or manifold body as described herein. The stamp or mold can be prepared to define all the features of the device. Also, the chambers can include collagen or matrigel or other gelatinous cell culture scaffold material. Also, electrospun fibers can be used for the scaffolds.

In one embodiment, a cell culture device can include a plurality of multi-chambered cell culture wells. That is, a well plate can include a plurality of wells configured with the multiple chambers. The wells can be engineered with appropriate inlets and outlets as described herein. The plates may include microfluidic pathways between the wells. For example, a well plate of a standard size that fits in a plate reader having 96 wells can be configured to include the microfluidic networks in one or more wells or in each of the wells. For example, a single cell culture device or single microfluidic network can be configured with two or more different organ simulations, which may be separate or linked in a biologically relevant series.

The microfluidic pathways and/or tissue chambers can have distinct cell cultures. The cells can be any type of cell ranging from immortalized cell lines to primary cells from patients. In some instances, a tissue culture from a patient can be included in a distinct chamber. The cell cultures can include a single type of cell or a combination of cells, such as two, three, or four different types in a co-culture. In some natural tissues, multiple cells may be present, and such tissues can be simulated with a similar cell type combination.

The common flow paths or inlets and/or outlets of the microfluidic networks of the cell culture device may be connected to a flow or pressure regulating system that can regulate the pressure across the distinct chambers or within each distinct chamber. Pumps and valves can be used to regulate the pressure. As such, operation of the device can include regulating the pressures inside each of the tissue chambers. For example, in a tissue such as the liver or the kidneys that may be leaky, pressure control can be used to simulate such leakiness of the tissue. Also, some tissue like the brain can have very high pressures, which can be simulated with controlling the pumps and valves. The system can regulate the pressure in each of these distinct tissue chambers as desired.

The pressure can be selectively controlled by the valves under operation of a control system. The control system can include a memory device having computer-executable instructions for selectively controlling valves of the device in order to regulate pressure. The valves can be prepared from the same or different materials as the body of the device, or they can be separate materials that are inserted into ports in the device at discrete locations. Each discrete microfluidic pathway or tissue chamber thereof can have one or more valves for pressure regulation which may be located in the top wall or as illustrated. Two valves can be used as an inlet and an outlet of a microfluidic pathway or tissue chamber thereof, as illustrated. The device may include a fluid pathway inlet and outlet with valves for a microfluidic pathway, as well as a pressure inlet valve and pressure outlet valve for each tissue chamber. Fluid pathway valves can regulate fluid flow, while the pressure valves can regulate pressure within the chambers.

The cell culture device can be used for any purpose involving cell culture. The cell culture device can be used in cell culture methods to simulate an organ. The methods can include testing one or more analytes for a presence or absence of biological response from a simulated biological fluidic pathway or organ. The biological response can be from the one or more analytes modulating a biological pathway, cell function, metabolic function, or toxicity. Any of the studies described herein or in the incorporated references can be performed with the multi-chambered cell culture device.

The device can be used to test the effect of any substance on the cells or simulated organ of the microfluidic pathways, and vice versa. The substance can be a biologically active agent that can be any agent that is administered for a function, such as a biological function to improve or otherwise modulate a biological process, such as a biological pathway. However, the agent can be active, such as to emit light, without being biologically active. As such, the biologically active agent can be a traditional pharmaceutical or nutraceutical, and it can be any type of substance for testing or diagnostics. The biologically active agent can be any agent that is administered to a subject in order to elicit a biological response that arises from the biological activity of the agent. The biological response obtained can be a measurable biological response or provide some change that can be analyzed and determined, such as by testing to determine an amount of the biologically active agent to be administered. The biologically active agent can be a toxin or poison or other deleterious substance. Examples can include the biologically active agent being a mineral, vitamin, pharmaceutical, nutraceutical, small molecule, macromolecule, organic molecule, polypeptide, protein, nucleic acid, polynucleotide, derivatives thereof, and combinations thereof. The biologically active agent can be for a human or animal subject. Human and veterinary medicines can be improved with the present invention. The substance can be an agricultural agent which can include herbicides, pesticides, and/or fertilizers. The substance can be an environmental substance that is natural or manmade and found in the environment. The substance can be a particle. The substance can be a foreign cell not found in an organ, such as a cancer cell, bacteria, yeast, or the like, and even a virus. The test substance can be a particle, such as a nanoparticle, liposome, microparticle, or microsphere or any other similar type of particle.

Figure 16:
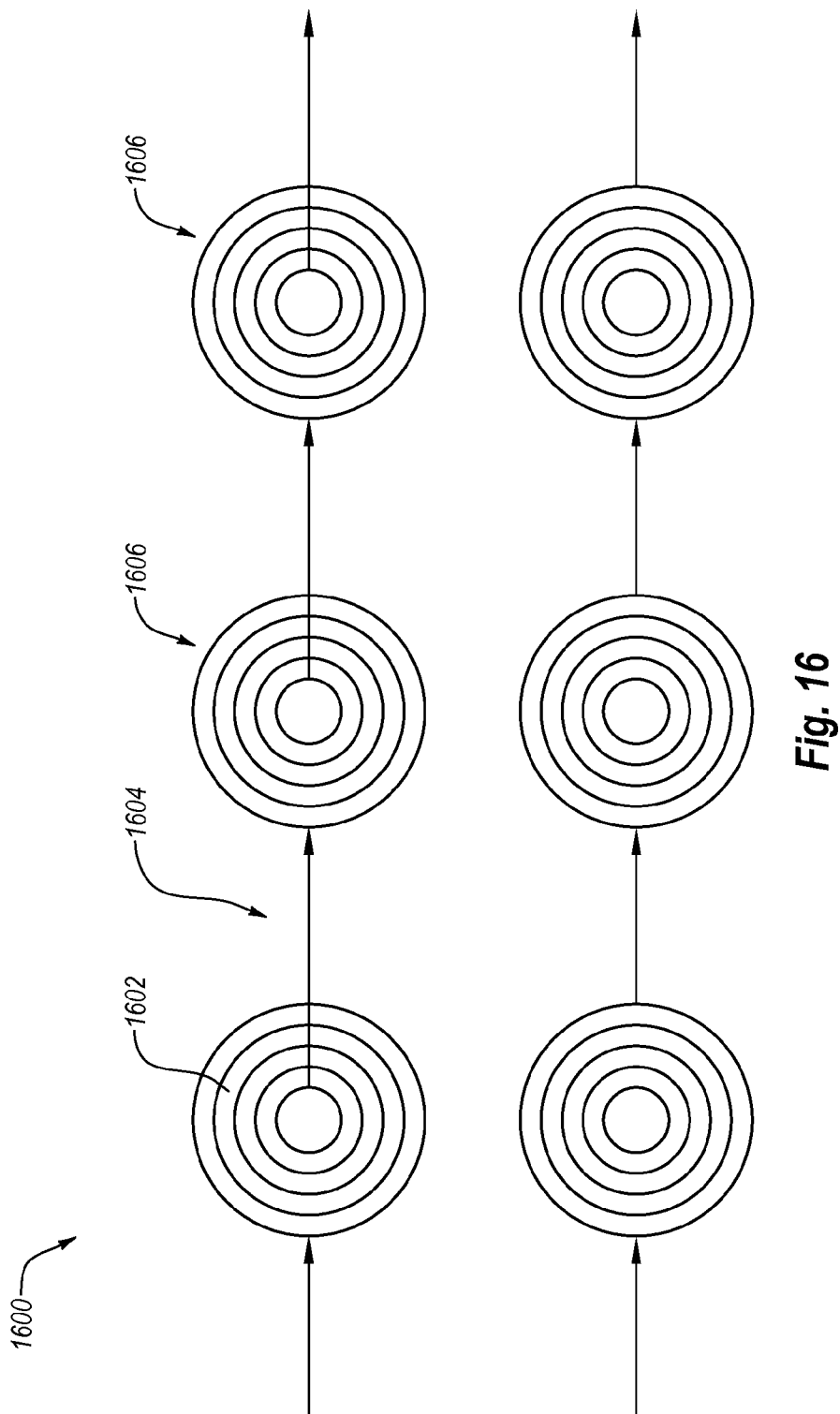
FIG. 16 illustrates an embodiment of an assay apparatus having multi-chambered organ simulation chambers.
Figure 17:
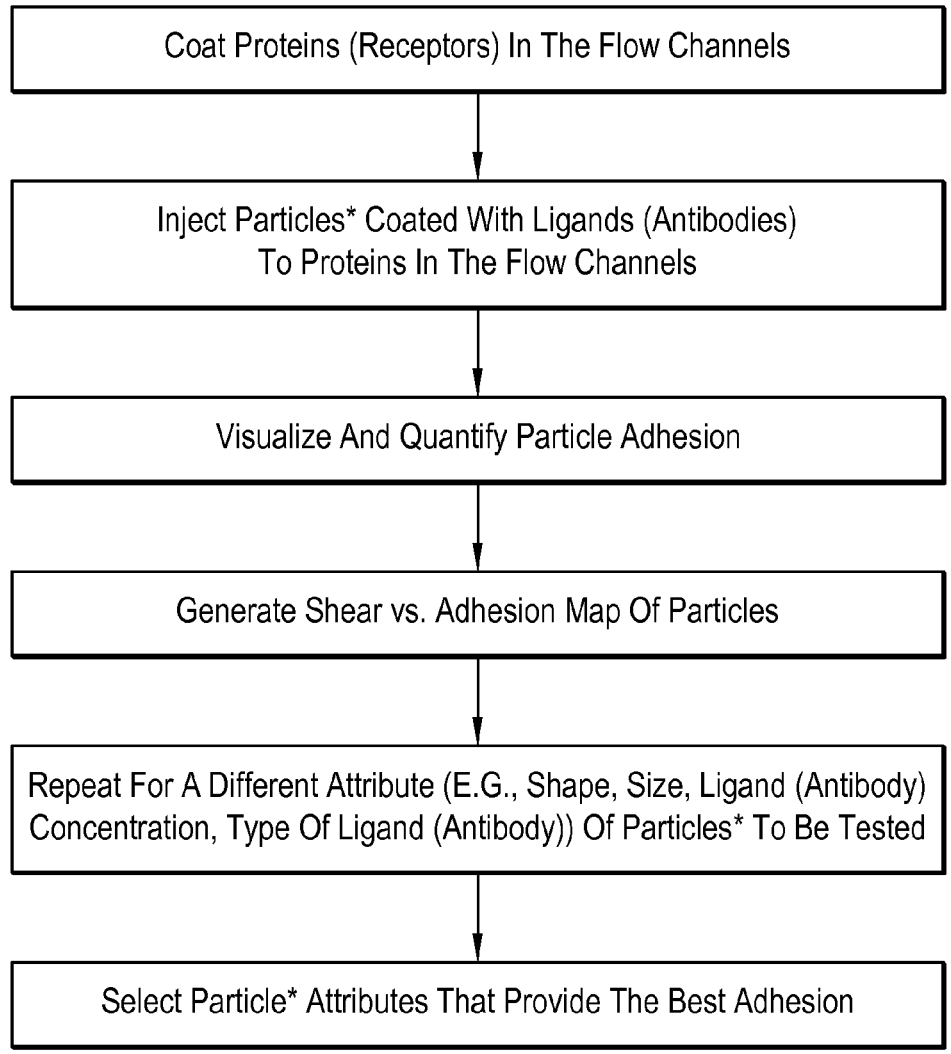
FIG. 17 includes a flow diagram showing assay steps that can be implemented with the assay apparatus of the invention.

FIG. 16 shows an embodiment of an assay apparatus 1600 having multi-chambered cell culture constructs 1602. The apparatus includes a first distinct microfluidic network 1604 that includes an assay region 1606 including multi-chambered cell culture constructs 1602. Each multi-chambered cell culture construct can include a synthetic or idealized internal organ tissue chamber, one or more boundary layers separated from the internal organ tissue chamber by one or more porous walls, and an outer conduit chamber separated from the one or more boundary layer conduits by one or more porous walls. The contents of an internal organ tissue chamber can be transferred to the outer conduit chamber of the next serial multi-chambered cell culture construct 1602, or the contents of an outer conduit chamber can be transferred to the outer conduit chamber of the next serial multi-chambered cell culture construct 1602. Each internal organ tissue chamber, one or more boundary layers, and/or outer conduit chamber can include its own manifold and inlets and outlets as described herein.

In one embodiment, the microfluidic chips can include a multi-chambered cell culture device that can provide improved organ models as well as methods of making and using the same. The multi-chambered cell culture device can include an outer chamber that can be used as an outer conduit and an internal chamber that can be used as an internal organ tissue space separated by one or more barrier chambers (e.g., barrier layer chambers). As such, the multi-chambered cell culture device can be a construct with an outer chamber and a central chamber separated by one or more barrier chambers therebetween. The multi-chambered cell culture device can include one or more of the outer chambers, one or more barrier chambers, and the central chamber being a cell culture chamber. The multi-chambered cell culture device can include one or more of the outer chambers, one or more barrier chambers, and the central chamber being devoid of cell cultures. The multi-chambered cell culture device can include an outer conduit (e.g., outer chamber) and an internal organ tissue space (e.g., central chamber) separated by one or more barrier layers (e.g., barrier chambers). In one aspect, an internal organ tissue space (e.g., central chamber) may be offset or off-center or asymmetrical with respect to the outer chamber and barrier chambers, and thereby may be referenced as an internal chamber that is surrounded by the barrier chambers that are surrounded by the outer chamber. This provides the chambers in an onion layer arrangement.

The conduit, organ tissue space, and one or more organ barrier layers can be distinct chambers that are partitioned from each other with porous walls. The porous walls can have true pores or have gaps between wall sections or gaps between barrier pillars or posts that function as pores so that fluid and nutrients and test analytes can pass between the distinct chambers. In one option, the pores can be gaps that are large enough for cancer cells to pass therethrough, such as for cancer metastasis modeling or for cell migration. The porous walls can be configured to keep the chambers distinct from each other while the pores in the porous walls can allow for nutrients to move therebetween. This configuration can provide for modeling of an organ.

Generally, any of the chambers, such as the outer chamber, inner chamber, boundary layer chambers, inner organ tissue space chamber, one or more organ barrier layers, or other distinct region in the multi-chambered construct can be distinct chambers that are partitioned from each other with porous walls and used for tissue culture spaces. For example, the outer chamber and/or any barrier chamber and/or any combination thereof with or without the internal chamber can be used as a tissue culture chamber. Oppositely, the outer chamber and/or any barrier chamber and/or any combination thereof with or without the central chamber can be used without having any cell culture therein.

The multi-chambered cell culture device can include a fluid inlet and fluid outlet for each of the distinct chambers. The fluid inlets and outlets can be adjacent or distributed about the device, or random on the device. The fluid outlet of one device can be fluidly coupled to the inlet of another device so that multiple simulated organs can be linked. For example, a metabolic pathway or organ series can be mimicked by linking multiple devices through their inlets and outlets. For example, a series of simulated organ devices can be lung, liver, heart, and kidney. The linked devices may be in series and/or in parallel (see FIG. 18), and may be linear or may include branches (see FIGS. 18 and 19). For example, a liver device may be fluidly coupled to a downstream brain device and a kidney device. As such, the fluid inlets and outlets can be bifurcated. Such bifurcations can be idealized (e.g., IMN) or synthetic (e.g., SMN). The multi-chambered cell culture device can include one or more IMN or SMN networks coupled to one or more of the inlets.

Figure 18:
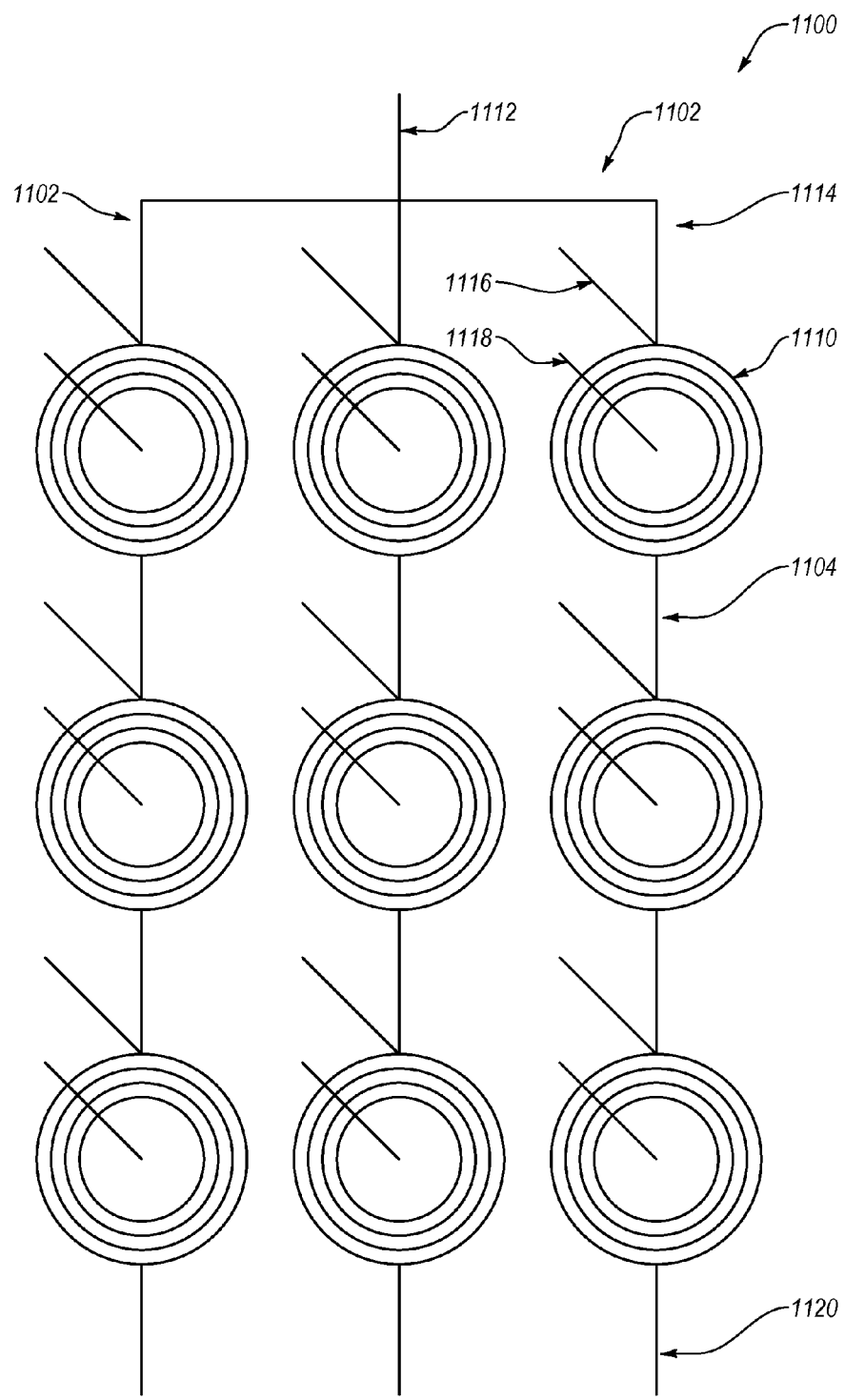
FIG. 18 illustrates an embodiment of a network showing parallel and/or series multi-chambered cell culture constructs.

FIG. 18 shows a network 1100 having multi-chambered constructs 1110 in parallel and series. Any of connecting fluid pathways 1104 are optional. While a single inlet 1112 is shown for parallel analysis, each chain 1102 can include its own inlet 1114, and each multi-chambered construct 1110 can include its own inlet 1116 and a central port 1118. The central port 1118 can be an inlet or outlet. The network 1100 can have individual outlets 1120 for each chain 1102; however, the outlets 1120 may be fluidly coupled into a single outlet in some instances. Any of the inlets 1116 or the central ports 1118 can be optional. Also, the inlet 1112 and the outlets 1120 may be inverted. This network may be IMN or SMN. The network 1100 can be included in the microfluidic devices described herein, such as in FIGS. 10A, 10B and 11.

Figure 19:
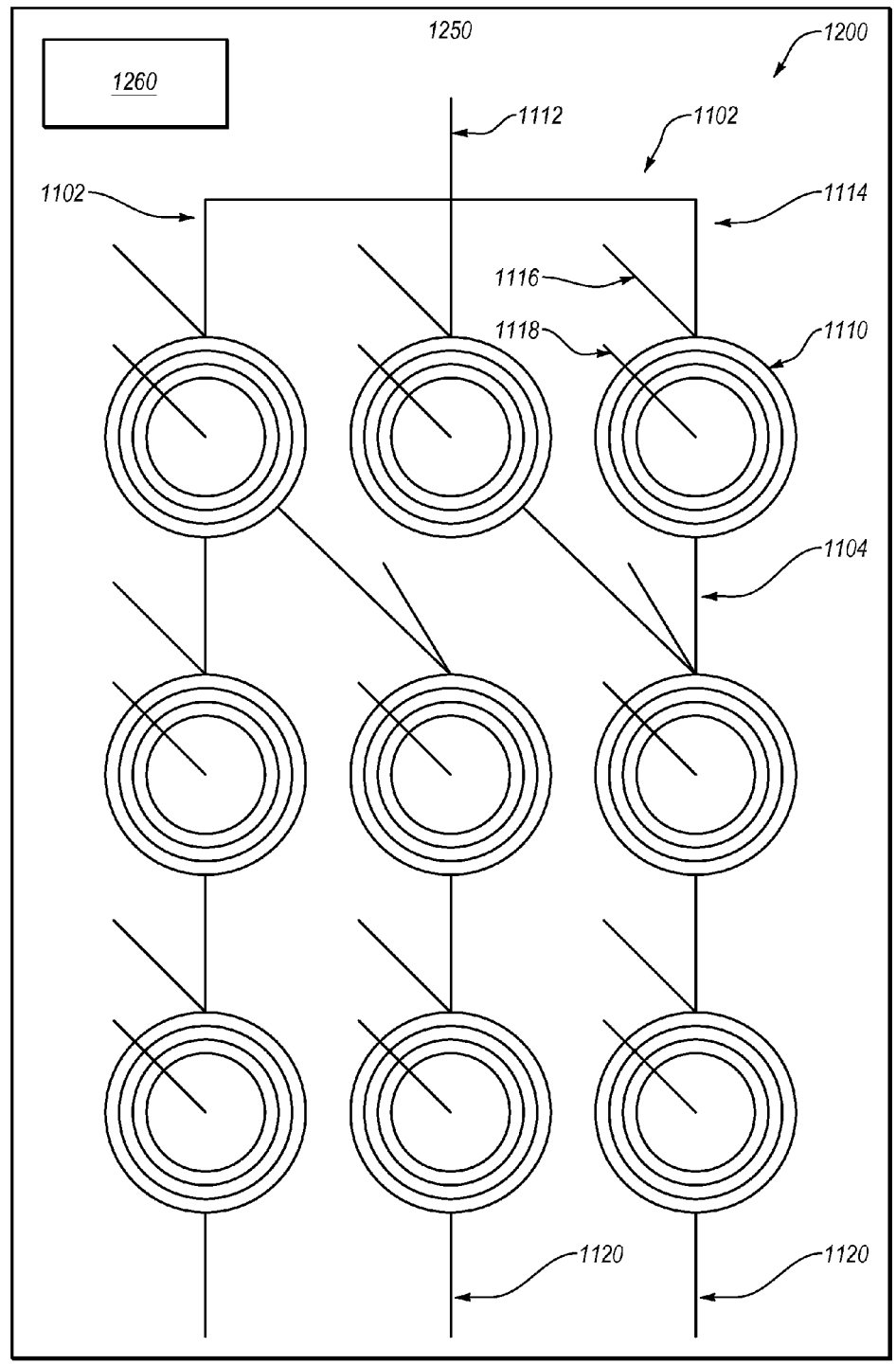
FIG. 19 illustrates an embodiment of parallel and series multi-chambered cell culture constructs having bifurcated outlets and joining inlets.

FIG. 19 includes a network 1200 having multi-chambered constructs 1110 in parallel and series. The connecting fluid pathways 1104 are shown so that the left chain includes a first multi-chambered construct 1110 with the outlet fluidly coupled with two multi-chambered constructs 1110 that are then each coupled to a single multi-chambered construct 1110. The right chain 1102 shows two first multi-chambered constructs 1110 with their outlets fluidly coupled with the single multi-chambered construct 1110 that is then coupled to the single multi-chambered construct 1110. This shows that any network arrangement of a plurality of multi-chambered constructs in parallel and/or series can be constructed, where inlets and outlets can be bifurcated, joined, branched, or other configuration in accordance with the description herein and in the incorporated references. The network 1200 can be included in the microfluidic devices described herein, such as in FIGS. 10A, 10B and 11.

In one embodiment, the distinct chambers can have different cells or cell combinations for different cell cultures. The cell culture of each chamber can have a distinct function. For example, the outer chamber can have endothelial cells and simulate the outside of an organ, the barrier layer conduits can have cells that simulate the barrier layers of an organ, and the internal chamber can have cells that simulate the functionality of the organ.

The internal walls between the vascular pathways and tissue chambers can be porous so that fluid and/or nutrients can pass therebetween. In one option, the pores can be a dimension that is too small for cells to pass through; however, the pores can be enlarged in some embodiments so that cells may pass therethrough such as when modeling cancer cell migration or metastasis. In any event, various analytes, such as test analytes and metabolic analytes, can pass through the pores of the porous walls. For example, the dimension of the pores can have a dimension up to 50 microns and as small as 100 nm; however, the dimension can range from about 200 nm to about 30 microns. The larger pores can be for cancer tissue modeling and allow for metastasis or cancer cells migrating between chambers. Generally, the pores can be smaller than 20 microns or smaller than 10 microns to control cell migration therethrough.

Each extravascular space or chamber can provide a tissue space that includes tissue culture scaffolds that will help grow the cells in a 2-D monolayer or in a 3-D sense to substantially fill up the entire space of the chamber. In the absence of the scaffolds, the cells will just cover the walls (e.g., bottom, sides, and/or top). Whereas the tissue scaffolds provide a 3-D cell culture in a nice, packed structure in the tissue space, the scaffolds can be the same or different material from the walls. The scaffolds can be integrated or coupled with the walls, or inserted into the chambers. The scaffolds can be cast in the same method when the walls of the chambers are cast.

The microfluidic devices can be manufactured in accordance with known principles, such as in the incorporated references. The devices can be made by providing a master and then pouring a polymer over it, then baking or otherwise curing the polymer so the polymer hardens, and then peeling the polymer from the master (e.g., mold). There can be a negative of the device on the master, which provides the device when cast with the polymer. The device can then be attached to a top wall, such as polymer or glass. The stamp or mold can be prepared to define all the features of the device. Also, the chambers can include collagen or matrigel or other gelatinous cell culture scaffold material. In addition, natural or synthetic culture scaffolds can be used. Also, electrospun fibers (comprising of culture matrix, proteins, and other biological and artificial components) can be used for the scaffolds. Cells can be mixed with scaffolds or cultured on scaffolds for creating a 2-D or 3-D culture.

In one embodiment, a substrate or plate can include a plurality of microfluidic chips having wells. The wells can be engineered with appropriate inlets and outlets as described herein. The plate may include the inlets and outlets between the wells. For example, a well plate of a standard size that fits in a plate reader having 96 wells can be configured to include a microfluidic chip in one or more wells or in each of the 96 wells. Well plates with smaller numbers of wells may also be prepared.

The extravascular chambers can have distinct cell cultures. The cells can be any type of cell ranging from immortalized cell lines to primary cells to patient-derived cells. In some instances, a tissue culture from a patient can be included in a distinct chamber. The cell cultures can include a single type of cell or a combination of cells, such as two, three, or four different types in a co-culture. In some natural tissues, multiple cells may be present, and such tissues can be simulated with a similar cell type combination.

The microfluidic chips may be connected to a flow or pressure regulating system that can regulate the pressure across the vascular pathways and distinct chambers or within each distinct chamber. Pumps and valves can be used to regulate the pressure. As such, operation of the device can include regulating the pressures inside each of the pathways or chambers. For example, in a tissue such as the liver or the kidneys that may be leaky, pressure control can be used to simulate such leakiness of the tissue. Also, some tissue like the brain and tumor can have very high pressures, which can be simulated with controlling the pumps and valves. The system can regulate the pressure in each of these distinct chambers of the microfluidic chips as desired to mimic normal vs. diseased conditions.

The pressure can be selectively controlled by valves under the operation of a control system (FIG. 12). The control system can include a memory device having computer-executable instructions for selectively controlling valves of the device in order to regulate pressure. The valves can be prepared from the same or different materials as the body of the device, or they can be separate materials that are inserted into ports in the device at discrete locations. Each discrete vascular pathway or extravascular chamber can have one or more valves for pressure regulation, which may be located in the well. Two valves can be used as an inlet and an outlet, as illustrated. The device may include a fluid pathway inlet and outlet with valves as well as a pressure inlet valve and pressure outlet valve in wells. Fluid pathway valves can regulate fluid flow, while the pressure valves can regulate pressure within the chambers of the microfluidic chips.

The microfluidic chips, plurality thereof, and device having the same can be used for any purpose involving cell culture. The microfluidic chips can be used in cell culture methods to simulate an organ. The methods can include testing one or more analytes for a presence or absence of biological response from the simulated organ. The biological response can be from the one or more analytes modulating a biological pathway, cell function, metabolic function, or toxicity. Any of the studies described herein or in the incorporated references can be performed with the microfluidic chips.

The test substance can even be a substance commonly used in a pharmaceutical product or combination thereof to test for activity in certain simulated organs. The test substance can include the following: a film-forming agent, a filler, a plasticizer, a taste-masking agent, a coloring agent, a solubilizing agent. an effervescent agent, an antioxidant, an absorption enhancer, a disintegrating agent, a pH modifying or buffer agent, a surfactant, a complexing agent, a bioadhesive agent, a sheet adhesive, an identifying agent, an anti-counterfeiting agent, a tracking agent, transporter inhibitor agent, transporter inducer agent, emulsifying agent, self-emulsifying system agents, crystallization inhibitor, crystallization promoter, supersaturation promoting agent, antimicrobial preservative, catalyst, chelating agent, particles, organoleptic agent, flavoring agent, scent agent, identifying device, and/or anti-counterfeiting device.

In one embodiment, cells can be analyzed in any of the wells. However, in some assays, only the cells in the wells having microfluidic chips with extravascular spaces will be assayed. For example, visual analysis, such as with a microscope, can be used for analysis of the cells. In another example, the cells can be identified using optical or electrical methods. For example, cell staining markers specific for cell types can be used. In addition, electrical signals-based detection can allow detection of morphology changes (cell differentiation) and different types of cells.

The present invention provides apparatus and methods that can be used to study fluid flow and particle adhesion in physiological vessels including arterioles, capillaries, venules, and microvascular networks comprising any combination of the three. The same apparatus and methods can also be used to optimize drug delivery in the microvasculature.

Many drugs are available in microencapsulated, liposomal/lipisomal, and other micro and nanoscale particle forms. The adherence and uptake of these particles in the microvasculature depends on specific and nonspecific interactions between the surfaces of drug delivery particles and endothelial cells that line the walls of the microvasculature. Adhesion also depends on fluid dynamics parameters such as flow velocities and shear forces which, in turn, depend on vascular network geometries. The present invention provides microfluidic chips comprising synthetic microvascular networks (SMNs) with flow channels that possess key geometric and topological features that cause them to display the same types of fluid flow patterns and particle adhesion patterns as are found in physiological microvascular networks. In addition, the SMNs require quantities of reagents that are reduced by orders of magnitude compared with currently used techniques. Known microfabrication techniques also allow for development of plastic, disposable chips eliminating concerns of cross-contamination.

In a non-limiting example, a substrate with a plurality of microfluidic chips can be constructed using techniques employed in the semiconductor industry such as photolithography, wet chemical etching, thin film deposition, and soft lithography using polymeric substrates, such as Polydimethylsiloxane (PDMS). Other materials that may be used in place of PDMS include Poly(Styrene Butadiene Styrene) (SBS) and Poly(Styrene-Ethylene-Butadiene-Styrene) (SEBS) elastomers, Polyester-ether (PEE) thermoplast, and thermoset polyester (TPE), which can be used for replica molding fabrication techniques. Polyolefin plastomer (POPs) can be specifically used for submicron range channels. Glass or quartz with reactive wet/dry etching of the microchannels can also be used. Thermoplastic materials such as polymethylmethacrylate (PMMA), polycarbonate (PC), cyclic olefin copolymer (COC), polystyrene (PS), poly vinyl chloride (PVC), and polyethylene terephthalate glycol (PETG) can be used with embossing techniques or injection molding. PS, PC, cellulose acetate, polyethylene terephthalate (PET), PMMA, PETG, PVC, PC, and polyimide can also be used with laser ablation techniques. In general, a microfluidic chip is formed with a number of microchannels that are connected to a variety of reservoirs containing fluid materials. The fluid materials are driven or displaced within these microchannels throughout the chip using electrokinetic forces, pumps and/or other driving mechanisms. Other manufacturing techniques can be used.

Figure 20:
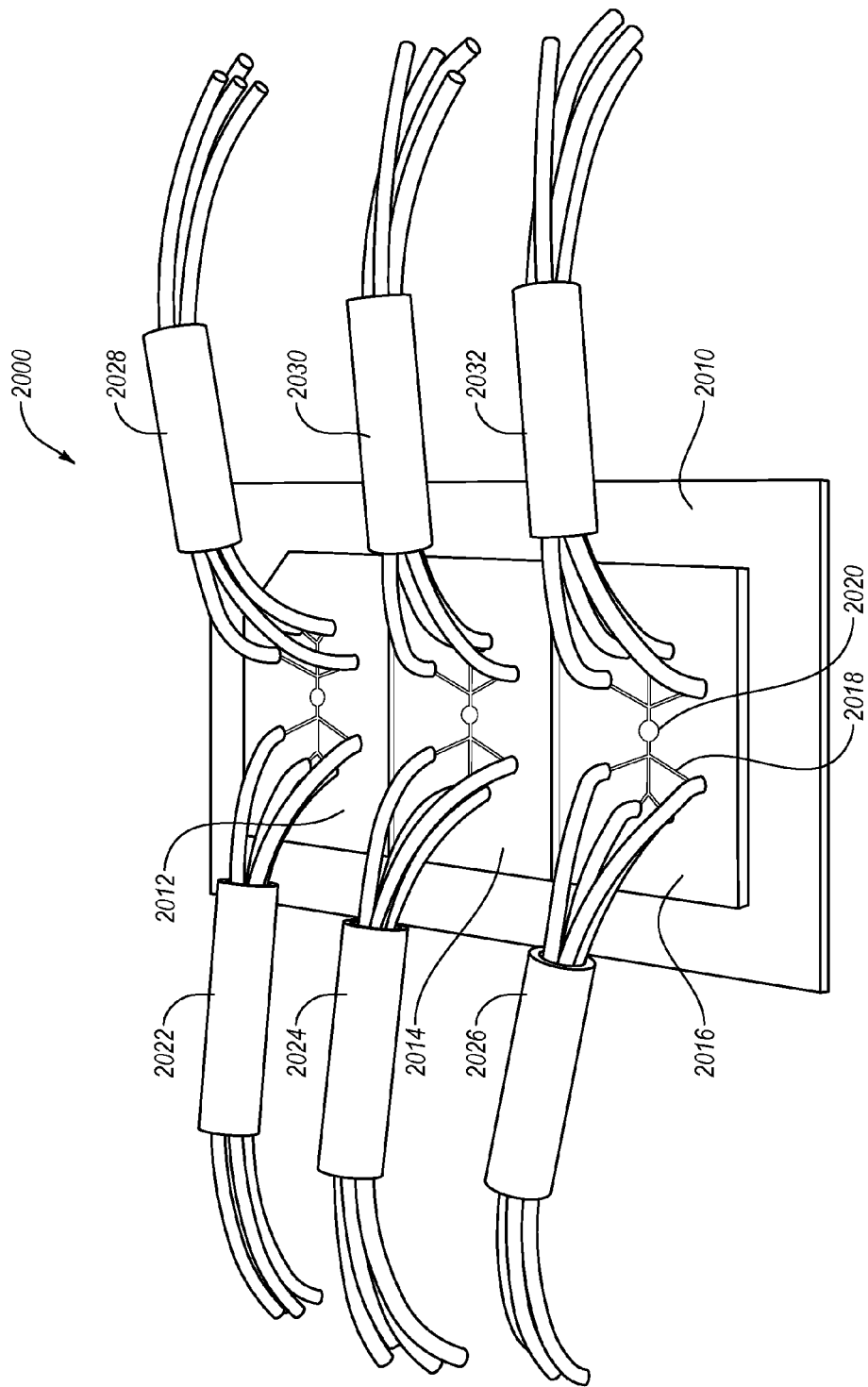
FIG. 20 illustrates an embodiment of a multiplexed assay device that includes a substrate having three separate microfluidic chips that are fluidly coupled with a manifold with inlet and outlet fluid tubes.
Figure 21:
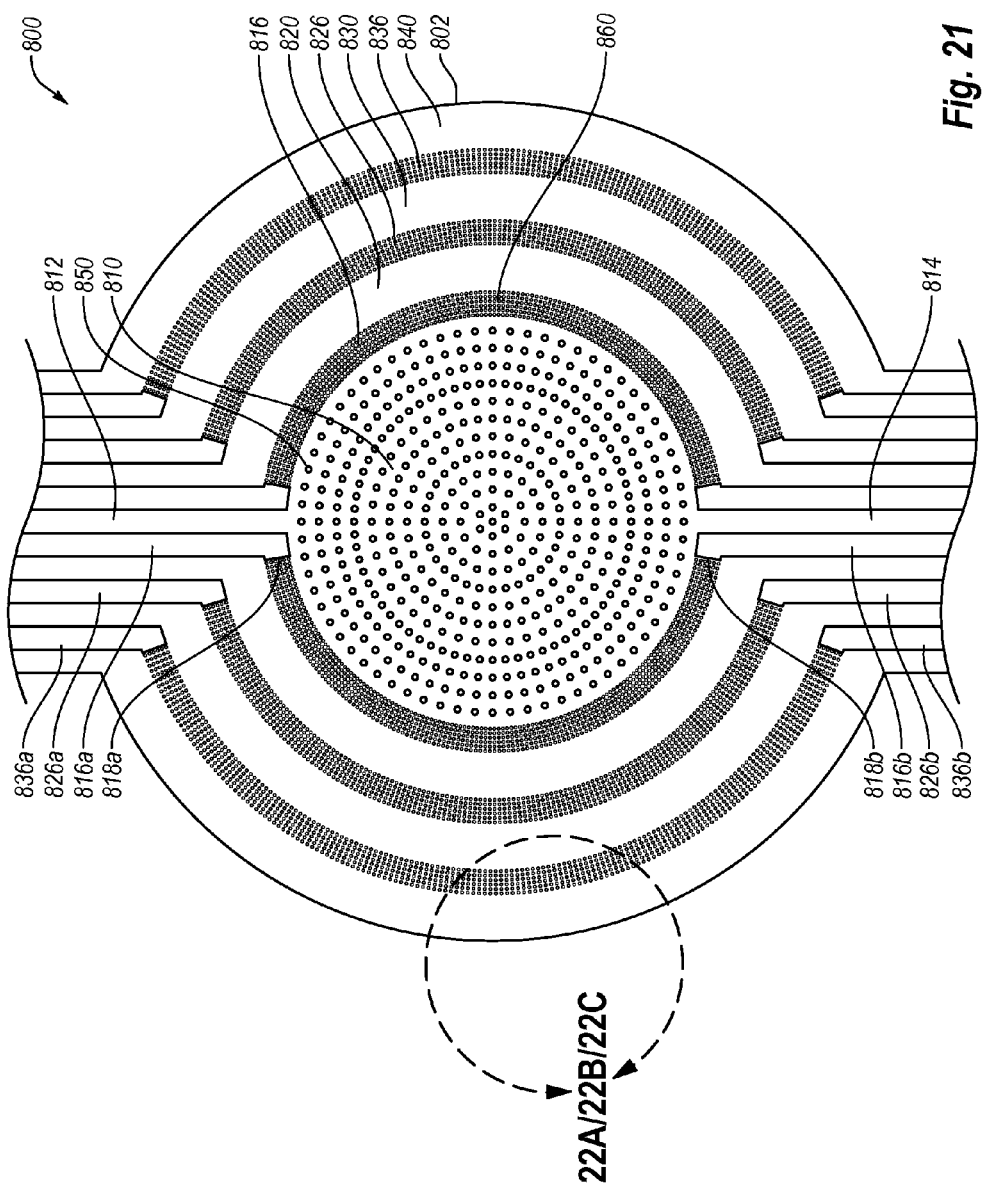
FIG. 21 illustrates an embodiment of a multi-chamber cell culture device with central chamber with internal pillars or posts and barrier pillars or posts forming porous walls between the chambers in an idealized configuration.
Figure 22A:
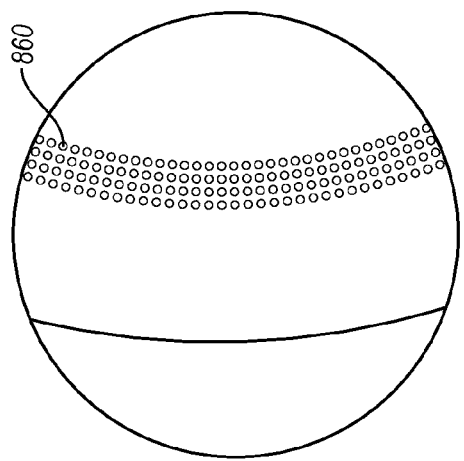
FIGS. 22A-22C illustrate different embodiments of barrier pillars or posts forming porous walls.
Figure 22B:
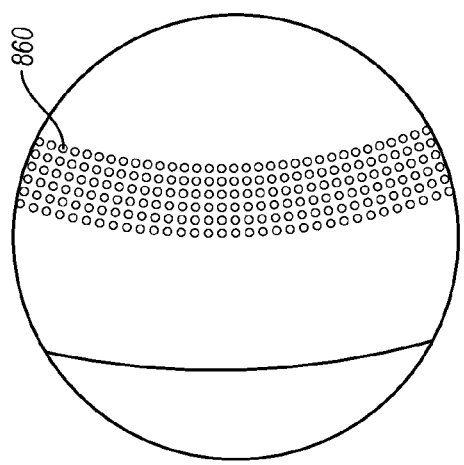
Figure 22C:
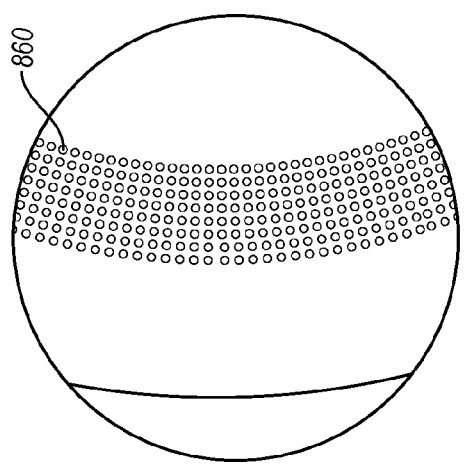

FIG. 20 illustrates an embodiment of a multiplexed assay device 2000. The multiplexed assay device 2000 includes a substrate 2010 having three separate microfluidic chips 2012, 2014, 2016. Each microfluidic chip includes vascular flow paths 2018 and a tissue space 2020, which can correspond with embodiments of FIGS. 8 and 9. The microfluidic chips 2012, 2014, 2016 are coupled to inlet manifolds 2022, 2024, 2026, each manifold having two inlet tubes operably coupled to the vascular flow paths 2018 and two inlet tubes operably coupled to the tissue space 2020. The microfluidic chips 2012, 2014, 2016 are also coupled to outlet manifolds 2028, 2030, 2032, each manifold having two outlet tubes operably coupled to the vascular flow paths 2018 and two inlet tubes operably coupled to the tissue space 2020. The features of the multiplexed assay device 2000 illustrate the operability of the device having a plurality of microfluidic chips. Each of the microfluidic chips 2012, 2014, 2016 can have different assays. The manifolds 2028, 2030, 2032 are shown to have tubes extending therefrom that can be coupled to fluid reservoirs, pumps, or other fluid devices. These tubes may be the same or different from those connected to the microfluidic chips 2012, 2014, 2016.

In one embodiment, an automated cell culture system 1250 (See FIG. 19) can include: the cell culture device having one or more multi-chambered constructs as described herein; and a computing system 1260 (see FIG. 19) operably coupled to the cell culture device and having a memory device with computer executable instructions for controlling fluid flow of the chambers independently. The computing system 1260 can be configured to control any valve in any chamber for automated cell culture methods for various assays. The computing system 1260 and automated cell culture system 1250 can be utilized with any of the embodiments of the invention described herein.

FIG. 20 shows another embodiment of a multi-chambered structure 800 in accordance with the principles of the present invention. Each microfluidic chip can include one or more of the multi-chambered cell culture devices 800. A well of the microfluidic chip can include the multi-chambered cell culture device 800. The multi-chambered cell culture device 800 is shown to include an internal chamber 810, an inner boundary layer chamber 820, an outer boundary layer chamber 830, and an outer conduit layer 840. However, only one boundary layer chamber or more than two additional boundary layer chambers can be located between the internal chamber 810 and outer conduit layer 840. The internal chamber 810 can include a fluid inlet 812 and a fluid outlet 814. The inner boundary layer chamber 820 can include at least one fluid inlet and at least one fluid outlet as described herein. The outer boundary layer chamber 830 can include at least one fluid inlet and at least one fluid outlet as described herein. The outer conduit layer 840 can include at least one fluid inlet and at least one fluid outlet as described herein. The internal chamber 810 can be defined by a porous tissue chamber wall 816, the inner boundary layer chamber 820 can be defined by the porous tissue chamber wall 816 and a porous boundary layer wall 826, the outer boundary layer chamber 830 can be defined by the porous boundary layer wall 826 and a porous outer conduit wall 836, and the outer conduit layer 840 is defined by the porous outer conduit wall 836 and an external wall 802 that is not porous. Here, the porous walls 816, 826, 836 can include a plurality of posts 860 that form the walls with the gaps between the posts 860. The porous walls 816, 826, 836 have one or more posts 860 laterally or radially oriented to form the walls. FIGS. 9A-9C show the porous walls can include any number of laterally or radially oriented posts 860 between chambers, where 4 posts, 6 posts, and 8 post embodiments are shown, but any number of posts 860 can be used as the porous walls, including a line of single posts 860 forming the porous walls 816, 826, 836.

In one embodiment, the porous walls 816, 826, 836 can be configured as conduits or chambers, and may include inlets 816a, 826a, 836a, and/or outlets 816b, 826b, 836b.

In one embodiment, the porous walls 816, 826, 836 are not conduits or chambers, and are configured as barrier walls. Here, the porous walls 816, 826, 836 may be devoid of inlets 816a, 826a, 836a, and/or outlets 816b, 826b, 836b. As shown for porous wall 816, an inlet barrier wall 818a and/or outlet barrier wall 818b can be included.

It should be recognized that the porous walls having the one or more lateral or radial posts, post array, post line, or any other orientation or distribution of posts 860 can be applied to any of the barrier walls between any of the chambers/conduits of any of the other embodiments or figures herein. The posts can have an even spacing therebetween or asymmetrical spacing. The posts can be uniform in size or have size distributions along a pathway or chamber or through the wall from one chamber to anther chamber.

In one embodiment, any of the chambers/conduits can include structure posts 850 that can be used to provide structure between top walls (e.g., well plate) and bottom walls (e.g., substrate). However, the posts may only be attached to the bottom substrate and may have a free top end when located in a well. The structure posts 850 can be coupled to a bottom wall, and may be coupled to a top wall when integrated with the side walls. Also, the top wall as a lid, such as the well plate, can rest on the structure posts 850. The structure posts can be used for cell culture, and can result in a higher cell density for organ simulations. FIG. 20 shows the central chamber 810 as having the posts 850, but it can be devoid of posts. Any of the boundary chambers 820, 830 can include the posts 850 or be devoid of posts. The outer chamber 840 can include the posts 850 or be devoid of posts.

In one embodiment, a cell culture assay device can include a substrate having a plurality of discrete microfluidic networks and a plurality of wells over the discrete microfluidic networks, each discrete microfluidic network having one or more wells fluidly coupled thereto, the wells extending upward from the discrete microfluidic networks, and a manifold body coupled with the substrate and having at least one fluid conduit pair for each microfluidic network and/or each well, each fluid conduit pair including a fluid inlet conduit and a fluid outlet conduit fluidly coupled to a corresponding microfluidic network and/or well.

In one aspect, each discrete microfluidic network has at least one assay region, the plurality of assay regions being arranged in an array on the substrate. In one aspect, the assay regions are arranged in rows and/or columns on the substrate. In one aspect, the assay regions are positioned on the substrate to correspond in location to the wells, the wells being arranged to form a multi-well plate such that the assays can be assayed with a multi-well plate reader. In one aspect, the assay regions are each contained within a well, the substrate having a grid array of wells in columns and/or rows. In one aspect, the wells are distributed in accordance with a multi-well plate reader configured to read each well. In one aspect, the substrate has a grid array of wells arranged in rows and/or columns, a plurality of the wells containing at least a portion of a discrete microfluidic network. In one aspect, the substrate has three, six, 12, 24, 36, 72, 96, 384, or 1536 wells, a plurality of the wells include at least a portion of the discrete microfluidic networks. In one aspect, only one entire distinct microfluidic network is contained within a distinct well of the substrate. In one aspect, a single distinct microfluidic network extends across two or more distinct wells of the substrate. In one aspect, a single distinct microfluidic network includes at least two assay regions in different distinct wells. In one aspect, a first assay region is entirely contained within a first distinct well.

In one embodiment, a first distinct microfluidic network includes a first assay region including at least one of a synthetic microvascular network, an idealized microvascular network, a synthetic tissue chamber, an idealized tissue chamber, or multi-chambered cell culture construct having a synthetic or idealized central chamber, one or more boundary layers separated from the central chamber by one or more porous walls, and an outer conduit chamber separated from the one or more boundary layer conduits by one or more porous walls. A synthetic tissue chamber can include features of a SMN, where the features are not idealized or having straight walls or linear conduits. An idealized tissue chamber can include features of an IMN, where the features are idealized and include straight walls or linear conduits. In one aspect, each synthetic or idealized tissue chamber is distinct and fluidly coupled to a microfluidic conduit through one or more porous walls. In one aspect, each synthetic or idealized tissue chamber is only fluidly coupled to a microfluidic conduit through one or more porous walls. In one aspect, one or more assay regions each include a distinct tissue chamber. In one aspect, each tissue chamber is associated with only one well of the substrate.

In one embodiment, a first distinct microfluidic network includes at least one fluid supply reservoir operably coupled with a fluid inlet conduit, wherein each fluid supply reservoir is associated with a distinct well of the substrate. In one aspect, a first distinct microfluidic network includes at least one waste fluid reservoir operably coupled with a fluid outlet conduit, wherein each waste fluid reservoir is associated with a distinct well of the substrate.

In one embodiment, a first discrete microfluidic network includes at least one fluid supply reservoir in a first distinct well of the substrate, at least one assay region in a second distinct well of the substrate, and one or more microfluidic pathways connecting the at least one fluid supply reservoir with the at least one assay region, the one or more microfluidic pathways extending between the first and second distinct wells of the substrate.

In one embodiment, a first discrete microfluidic network includes two or more tissue chambers, each tissue chamber being in different wells of the substrate and linked together with microfluidic pathways extending between the different wells. In one aspect, two or more tissue chambers are configured to simulate two or more different organs. In one aspect, a microfluidic pathway between the two distinct tissue chambers has an inlet at a first tissue chamber configured to simulate a first organ and an outlet at a second tissue chamber configured to simulate a different second organ.

In one embodiment, two or more tissue chambers are configured as two or more organs, and linked in a series that simulates a physiological organ series. In one embodiment, the organ series includes brain, liver, heart, kidney, lung, stomach, intestines, pancreas, ovary, cervix, spleen, arteries, venules, capillaries, and stem cells. In one aspect, three or more tissue chambers are linked together, each tissue chamber being in different wells of the substrate and simulating different organs.

In one embodiment, a first tissue chamber is linked to two downstream tissue chambers in parallel. In one aspect, a first microfluidic network extends across two or more wells of the substrate in a row and/or column. In one aspect, each distinct microfluidic network is substantially identical. In one aspect, two or more distinct microfluidic networks are substantially identical. In one aspect, two or more distinct microfluidic networks are substantially different. In one aspect, each distinct microfluidic network is substantially different. In one aspect, a row of microfluidic networks are substantially identical. In one aspect, a column of microfluidic networks is substantially identical. In one aspect, microfluidic networks in a row or a column of microfluidic networks are each substantially different.

In one embodiment, the distinct microfluidic networks are not interconnected with each other through microfluidic flow paths in the substrate.

In one embodiment, two or more of the distinct microfluidic networks are interconnected with each other through one or more microfluidic flow paths coupled to the fluid inlet conduits and/or fluid outlet conduits in the manifold body.

In one embodiment, each discrete microfluidic network has at least one assay region positioned in a well and under and coupled to the corresponding fluid inlet conduits and/or fluid outlet conduits in the manifold body. In one aspect, the fluid inlet conduits and/or fluid outlet conduits are arranged in rows and/or columns in the manifold body. In one aspect, the fluid inlet conduits and/or fluid outlet conduits are positioned in the manifold body to correspond in location to the wells such that the assays can be assayed with a multi-well plate reader when the manifold body is attached and/or removed.

In one embodiment, the substrate is integrated with the manifold body. The substrate may include the well plate integrated with a substrate base with the well plate integrated with the manifold body. In one aspect, the substrate is removably coupled with the manifold body.

In one embodiment, the fluid conduit pairs are each contained within a distinct well of the substrate. In one aspect, the fluid conduit pairs are included in wells, the fluid conduit pairs including tubes that extend through the wells so as to be fluidly coupled with the microfluidic networks. In one aspect, the substrate has a grid array of distinct wells arranged in rows and/or columns, a plurality of the distinct wells containing a fluid conduit pair fluidly extended therein from the manifold body. In one aspect, the manifold has three, six, 12, 24, 36, 72, 96, 384, or 1536 distinct fluid conduit pairs arranged in a grid array and corresponding with wells of the substrate. In one aspect, the manifold includes a fluid conduit pair for each distinct well of the substrate. In one aspect, a first fluid conduit pair includes a fluid inlet conduit in one well and a fluid outlet conduit in a different well of the substrate. In one aspect, a single fluid conduit pair is in the same well of the substrate. In one aspect, a first assay region includes a fluid conduit pair. In one aspect, one of the fluid conduit inlet or fluid conduit outlet of a fluid conduit pair has a dead end and is not coupled to the microfluidic network.

In one embodiment, at least one fluid inlet conduit is fluidly coupled to a distinct fluid reservoir. In one aspect, each fluid inlet conduit in a row and/or a column is fluidly coupled to a common fluid reservoir. In one aspect, each fluid inlet conduit in a row and/or a column is fluidly coupled to a common fluid conduit that is coupled or couplable to a fluid reservoir. In one aspect, each fluid outlet conduit is fluidly coupled to a distinct fluid waste reservoir. In one aspect, each fluid outlet conduit in a row and/or a column is fluidly coupled to a common fluid waste reservoir. In one aspect, each fluid outlet conduit in a row and/or a column is fluidly coupled to a common fluid conduit that is coupled or couplable to a fluid waste reservoir.

In one embodiment, a well plate body is positioned between the substrate and manifold body, the well plate body having a well aperture defining a well fluidly coupled to the substrate being formed from the well plate body being coupled to a substrate base having the discrete microfluidic networks. In one aspect, the well plate body includes each well aperture defining the well associated with a well portion of the substrate. In one aspect, the fluid conduit pairs include tubes that extend from common fluid inlet conduits and common fluid outlet conduits to the microfluidic networks.

In one embodiment, the microfluidic networks include fluid pathways and/or tissue chambers that are coated with a substance and/or cell culture. In one aspect, each tissue chamber includes a cell culture. In one aspect, different microfluidic networks include different coatings and/or different cell cultures. In one aspect, different tissue chambers include different cell cultures. In one aspect, tissue chambers configured to simulate an organ include one or more cell types of that organ. In one aspect, the cell culture includes primary cells from a subject.

In one embodiment, the substrate is dimensioned to fit into and be read by a multi-well plate reader. In one aspect, the substrate and wells are configured and dimensioned in accordance with standards of the American National Standards Institute for microtiter plates. In one aspect, the substrate is about 5 inches by 3.33 inches. In one aspect, the substrate is transparent. In one aspect, the substrate is radiolucent.

In one embodiment, a cell culture system comprising the device having the microfluidic chips as described herein, one or more fluid reservoirs configured to be coupled with the fluid conduit pairs of the manifold body, and one or more pumps operably coupled to the plurality of microfluidic networks through the fluid conduits. In one aspect, one or more valves in fluid conduits are fluidly coupled with the fluid inlet conduits and/or fluid outlet conduits. In one aspect, a computing system is operably coupled to the cell culture device and having a memory device with computer-executable instructions for controlling fluid flow of the fluid inlet conduits and outlet independently.

In one embodiment, a method of culturing cells can include providing the device having the microfluidic chips as described herein introducing one or more cell types into each discrete location in a plurality of the microfluidic networks, introducing cell nutrients with the fluid inlet conduits, and removing cell waste with the fluid outlet conduits.

In one embodiment, a method of testing an analyte can include providing the device having the microfluidic chips as described herein, introducing one or more test analytes into a plurality of the microfluidic networks, incubating the one or more test analytes with cell cultures in the microfluidic networks, and determining whether or not the test analyte had an effect on the cell cultures. In one aspect, the method can include introducing the same test analyte into all microfluidic networks. In one aspect, the method can include introducing the same test analyte to all microfluidic networks in a row or column. In one aspect, the method can include introducing the same test analyte through a common fluid conduit to the fluid inlet conduits fluidly coupled thereto and into corresponding microfluidic networks. In one aspect, the method can include decoupling the manifold body from the substrate and assaying assay regions on the substrate.

In one aspect, the method can include inserting the substrate with or without the manifold body into a microplate reader. In one aspect, the method can include delivering a first analyte with the fluid inlet conduit to a first assay region and delivering a second analyte with the fluid outlet conduit to the first assay region.

Virtual experiments using Computational Fluid Dynamics (CFD) or other computational modeling allow the ability to optimize the experimental protocols. This procedure not only saves time but also reduces reagent consumption. CFD modeling can also be used to differentiate between perfusion based vs. diffusion based experiments in addition to determining the flow rate ranges for optimal cell growth and assays. CFD modeling can also drive design optimization of each of the conduits and layers of the device ranging from distance for diffusion, pore size, number of pores.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

This patent document incorporates by specific reference in their entirety the following patents and patent applications: U.S. Pat. No. 7,725,267; U.S. Pat. No. 8,355,876; U.S. Pat. No. 8,175,814; U.S. Pat. No. 8,380,443; U.S. Pat. No. 8,417,465; U.S. Pat. No. 8,589,083; U.S. 2010/0227312; PCT/US2013/072081; U.S. 2013/0101991; and U.S. 2013/0149735.

The invention claimed is:

1. A cell culture well plate device comprising:
   a bottom body portion forming a substrate having a plurality of discrete microfluidic networks;
   a middle body portion over the bottom body portion and forming a plurality of wells over the discrete microfluidic networks such that portions of each of the discrete microfluidic networks in the substrate form bottoms of the wells, each discrete microfluidic network having one or more wells there over and fluidly coupled thereto, the wells extending upward from the substrate and from the portions of discrete microfluidic networks; and a top body portion over the middle body portion and forming a manifold having at least one manifold inlet conduit network and at least one manifold outlet conduit network, the at least one manifold inlet conduit network being fluidly coupled with at least one fluid inlet conduit, each fluid inlet conduit being located within and extending into at least one of the plurality of wells, the at least one manifold outlet conduit network being fluidly coupled with at least one fluid outlet conduit, each fluid outlet conduit being located within and extending into the at least one of the plurality of wells, such that there is at least one fluid conduit pair in a common well for each microfluidic network and/or each well, each fluid conduit pair including one fluid inlet conduit and one fluid outlet conduit fluidly coupled to a corresponding microfluidic network and/or well.

2. The device of claim 1, wherein each discrete microfluidic network has at least one assay region, the plurality of assay regions being arranged in an array on the substrate.

3. The device of claim 1, wherein:
a single distinct microfluidic network extends across two or more distinct wells of the substrate; or
a single distinct microfluidic network includes at least two assay regions in different distinct wells.

4. The device of claim 2, wherein a first distinct microfluidic network includes a first assay region including at least one of:
a synthetic microvascular network;
an idealized microvascular network;
multi-chambered cell culture construct having a central chamber, one or more boundary layers separated from the central chamber by one or more porous walls, and an outer conduit chamber separated from the one or more boundary layer conduits by one or more porous walls.

5. The device of claim 4, wherein each synthetic or idealized tissue chamber is distinct and fluidly coupled to a microfluidic conduit through one or more porous walls.

6. The device of claim 2, wherein one or more assay regions each include a distinct tissue chamber.

7. The device of claim 1, wherein:
a first distinct microfluidic network includes at least one fluid supply reservoir operably coupled with a first fluid inlet conduit, wherein each fluid supply reservoir is associated with a distinct well of the substrate; or
a first distinct microfluidic network includes at least one waste fluid reservoir operably coupled with a first fluid outlet conduit, wherein each waste fluid reservoir is associated with a distinct well of the substrate.

8. The device of claim 1, wherein a first discrete microfluidic network includes:
at least one fluid supply reservoir in a first distinct well of the substrate;
at least one assay region in a second distinct well of the substrate; and
one or more microfluidic pathways connecting the at least one fluid supply reservoir with the at least one assay region, the one or more microfluidic pathways extending between the first and second distinct wells of the substrate.

9. The device of claim 1, wherein a first discrete microfluidic network includes two or more tissue chambers, each tissue chamber being in different wells of the substrate and linked together with microfluidic pathways extending between the different wells.

10. The device of claim 2, wherein each discrete microfluidic network has at least one assay region positioned in a well and under and coupled to the corresponding fluid inlet conduits and/or fluid outlet conduits in the manifold body.

11. The device of claim 1, wherein the substrate has a grid array of distinct wells arranged in rows and/or columns, a plurality of the distinct wells containing a fluid conduit pair fluidly extended therein from the manifold body.

12. The device of claim 1, wherein:
at least one fluid inlet conduit is fluidly coupled to a distinct fluid reservoir; and
each fluid outlet conduit is fluidly coupled to a distinct fluid waste reservoir.

13. The device of claim 1, wherein:
each fluid inlet conduit in a row and/or a column is fluidly coupled to a common fluid conduit of the at least one manifold inlet conduit network that is coupled or couplable to a fluid reservoir; and
each fluid outlet conduit in a row and/or a column is fluidly coupled to a common fluid conduit of the at least one manifold outlet conduit network that is coupled or couplable to a fluid waste reservoir.

14. The device of claim 1, the middle body portion comprising a well plate body between the substrate and a manifold body of the top body portion, the well plate body having a well aperture defining a well fluidly coupled to the substrate and being formed from the well plate body being coupled to the substrate having the discrete microfluidic networks, and wherein the top body portion forms a lid for the coupled well plate body and substrate.

15. The device of claim 1, wherein:
the microfluidic networks include fluid pathways that are coated with a substance and/or cell culture; and
each tissue chamber includes a cell culture.

16. The device of claim 1, wherein different tissue chambers include different cell cultures.

17. The device of claim 1, wherein the substrate is transparent or radiolucent.

18. A cell culture system comprising:
the device of claim 1;
one or more fluid reservoirs configured to be coupled with the at least one manifold inlet conduit network; and
one or more pumps operably coupled to the plurality of microfluidic networks through the at least one manifold inlet conduit network.

19. The cell culture system of claim 18, comprising:
one or more valves in fluid conduits that are fluidly coupled with the fluid inlet conduits and/or fluid outlet conduits; or
a computing system operably coupled to the cell culture device and having a memory device with computer-executable instructions for controlling fluid flow of the fluid inlet conduits and outlet independently.

20. A method of culturing cells, the method comprising:
providing a cell culture device of claim 1;
introducing one or more cell types into each discrete location in a plurality of the microfluidic networks;
introducing cell nutrients with the fluid inlet conduits; and
removing cell waste with the fluid outlet conduits.

21. A method of testing an analyte, the method comprising:
providing a cell culture device of claim 1;
introducing one or more test analytes into a plurality of the microfluidic networks;
incubating the one or more test analytes with cell cultures in the microfluidic networks; and determining whether or not the test analyte had an effect on the cell cultures.

22. The method of claim 21, comprising introducing the same test analyte to all microfluidic networks in a row or column.

23. The method of claim 21, comprising:
introducing the same test analyte through a common fluid conduit to the fluid inlet conduits fluidly coupled thereto and into corresponding microfluidic networks.

24. The method of claim 21, comprising:
delivering a first analyte with the fluid inlet conduit to a first assay region; and
delivering a second analyte with the fluid outlet conduit to the first assay region.

25. The device of claim 1, wherein each discrete microfluidic network includes a vascular fluid pathway or extravascular space having vascular cells and tissue cells together.

26. The device of claim 25, wherein the vascular cells are endothelial cells.

27. The device of claim 2, wherein each synthetic microvascular network or idealized microvascular network contains vascular cells and each synthetic tissue chamber and idealized tissue chamber contain tissue cells.

28. The device of claim 2, wherein each synthetic microvascular network or idealized microvascular network contains both vascular cells and tissue cells and each a synthetic tissue chamber and idealized tissue chamber contains both vascular and tissue cells.

* * * * *